(12) United States Patent
Blizzard et al.

(10) Patent No.: US 10,159,630 B2
(45) Date of Patent: Dec. 25, 2018

(54) TWO- AND THREE-COMPONENT SILOXANE AND RELATED COMPOUNDS AND COMPOSITIONS

(71) Applicant: KIMMERLING HOLDING GROUP, LLC, Marietta, GA (US)

(72) Inventors: John D. Blizzard, Midland, MI (US); Kirk Kimmerling, Marietta, GA (US); Joseph P. Rapp, Hilton Head Island, SC (US)

(73) Assignee: Kimmerling Holdings Group, LLC, Marietta, GA (US)

( * ) Notice: Subject to any disclaimer, the term of this patent is extended or adjusted under 35 U.S.C. 154(b) by 462 days.

(21) Appl. No.: 15/066,379

(22) Filed: Mar. 10, 2016

(65) Prior Publication Data

US 2016/0199266 A1    Jul. 14, 2016

Related U.S. Application Data

(63) Continuation of application No. 13/594,282, filed on Aug. 24, 2012, now Pat. No. 9,314,407.
(Continued)

(51) Int. Cl.
   *C04B 16/00*    (2006.01)
   *C04B 24/00*    (2006.01)
   (Continued)

(52) U.S. Cl.
   CPC ............. *A61K 6/083* (2013.01); *A01N 25/34* (2013.01); *A61K 6/00* (2013.01); *C07F 7/04* (2013.01);
   (Continued)

(58) Field of Classification Search
   CPC ................................ C06B 16/00; C06B 24/00
   (Continued)

(56) References Cited

U.S. PATENT DOCUMENTS 6,221,944 B1    4/2001    Liebeskind et al.
6,469,120 B1    10/2002   Elfersy et al.
(Continued)

FOREIGN PATENT DOCUMENTS

CN    2012800492433         8/2012
DE       102004028543 A1   12/2005
(Continued)

OTHER PUBLICATIONS

International Preliminary Report on Patentability dated Feb. 25, 2014 for International Application PCT/US2012/052295 filed Aug. 24, 2012 and published as WO 2013/028984 on Feb. 28, 2013 (Applicants—Kimmerling Holdings Group, LLC;Inventors—Blizzard et al.) (7 pages).
(Continued)

*Primary Examiner* — James E McDonough
(74) *Attorney, Agent, or Firm* — Meunier Carlin & Curfman LLC

(57) ABSTRACT

Compositions are disclosed that comprise at least one compound of formula IV:

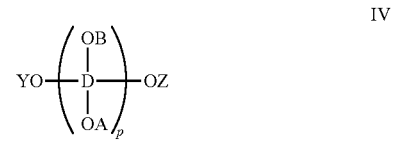

wherein the variable are as defined in the specification. The compositions are antimicrobial and optionally curable, and useful, inter alia, in dental, medical, and industrial applications for reinforcement and/or adhering two surfaces together.

17 Claims, 6 Drawing Sheets

Related U.S. Application Data

(60) Provisional application No. 61/635,047, filed on Apr. 18, 2012, provisional application No. 61/608,882, filed on Mar. 9, 2012, provisional application No. 61/579,464, filed on Dec. 22, 2011, provisional application No. 61/553,396, filed on Oct. 31, 2011, provisional application No. 61/548,091, filed on Oct. 17, 2011, provisional application No. 61/527,231, filed on Aug. 25, 2011.

(51) Int. Cl.
| | |
|---|---|
| A61K 6/083 | (2006.01) |
| A61K 6/00 | (2006.01) |
| C07F 7/04 | (2006.01) |
| A01N 25/34 | (2006.01) |
| C08F 265/06 | (2006.01) |
| C08F 267/06 | (2006.01) |
| C08F 283/10 | (2006.01) |
| C09D 5/14 | (2006.01) |
| C08G 77/58 | (2006.01) |
| C08G 77/26 | (2006.01) |
| C08L 83/08 | (2006.01) |
| C08L 83/14 | (2006.01) |
| C04B 12/04 | (2006.01) |
| C04B 28/26 | (2006.01) |
| C04B 35/16 | (2006.01) |
| C08G 77/14 | (2006.01) |
| C08G 77/20 | (2006.01) |

(52) U.S. Cl.
CPC .......... *C08F 265/06* (2013.01); *C08F 267/06* (2013.01); *C08F 283/10* (2013.01); *C08G 77/26* (2013.01); *C08G 77/58* (2013.01); *C08L 83/08* (2013.01); *C08L 83/14* (2013.01); *C09D 5/14* (2013.01); *C08G 77/14* (2013.01); *C08G 77/20* (2013.01); *Y10T 428/139* (2015.01)

(58) Field of Classification Search
USPC .......................................................... 106/600
See application file for complete search history.

(56) References Cited

U.S. PATENT DOCUMENTS

| | | | |
|---|---|---|---|
| 6,762,172 | B1 | 7/2004 | Elfersy et al. |
| 9,314,407 | B2 | 4/2016 | Blizzard et al. |
| 2006/0254469 | A1* | 11/2006 | Hirata ...................... C04B 24/32 106/805 |
| 2007/0065475 | A1 | 3/2007 | Elfersy |
| 2010/0093666 | A1* | 4/2010 | Moses .................... A01N 55/00 514/63 |

FOREIGN PATENT DOCUMENTS

| | | | |
|---|---|---|---|
| EP | 0957940 A1 | 11/1999 | |
| EP | 12756874.9 | 8/2012 | |
| HK | 15102389.8 | 3/2015 | |
| JP | 2004202925 A | 7/2004 | |
| JP | 2005255858 A | 9/2005 | |
| JP | 2007169507 A | 7/2007 | |
| WO | WO-2010/045454 A1 | 4/2010 | |
| WO | WO-2011/026093 A1 | 3/2011 | |
| WO | PCT/US2012/052295 | 8/2012 | |
| WO | WO-2013/028984 A1 | 2/2013 | |
| WO | WO-2013028984 A1 * | 2/2013 | ............. C08G 77/58 |
| WO | PCT/US15/054421 | 10/2015 | |
| WO | WO-2016/057630 A2 | 4/2016 | |

OTHER PUBLICATIONS

International Patent Application No. PCT/US2012/052295, International Search Report and Written Opinion, dated Nov. 15, 2012; 12 pages.
First Office Action issued by the State Intellectual Property Office of the People's Republic of China dated Oct. 19, 2015 for application CN 2012800492433, filed on Aug. 24, 2012 and published as CN 104066772 on Sep. 24, 2014 (Applicant—Kimmerling Holdings Group, LLC // Inventor—Blizzard, et al.) (6 pages—Translation).
Requirement for Restriction or Election dated Jun. 25, 2014 for application U.S. Appl. No. 13/594,282, filed Aug. 24, 2012 now U.S. Pat. No. 9,314,407 on Apr. 19, 2016 (Applicant/Inventor—Blizzard, et al.) (15 pages).
Response to Requirement for Restriction or Election filed on Aug. 25, 2014 for U.S. Appl. No. 13/594,282, filed Aug. 24, 2012 now U.S. Pat. No. 9,314,407 on Apr. 19, 2016 (Applicant/Inventor—Blizzard, et al.) (17 pages).
Second Requirement for Restriction or Election dated Oct. 23, 2014 for U.S. Appl. No. 13/594,282, filed Aug. 24, 2012 now U.S. Pat. No. 9,314,407 on Apr. 19, 2016 (Applicant/Inventor—Blizzard, et al.) (7 pages).
Response to Second Requirement for Restriction or Election filed on Dec. 22, 2014 for U.S. Appl. No. 13/594,282, filed Aug. 24, 2012 now U.S. Pat. No. 9,314,407 on Apr. 19, 2016 (Applicant/Inventor—Blizzard, et al.) (18 pages).
Non-Final Office Action dated Apr. 6, 2015 for U.S. Appl. No. 13/594,282, filed Aug. 24, 2012 now U.S. Pat. No. 9,314,407 on Apr. 19, 2016 (Applicant/Inventor—Blizzard, et al.) (7 pages).
Response to Non-Final Office Action dated Jul. 6, 2015 for U.S. Appl. No. 13/594,282, filed Aug. 24, 2012 now U.S. Pat. No. 9,314,407 on Apr. 19, 2016 (Applicant/Inventor—Blizzard, et al.) (17 pages).
Final Office Action dated Aug. 3, 2015 for U.S. Appl. No. 13/594,282, filed Aug. 24, 2012 now U.S. Pat. No. 9,314,407 on Apr. 19, 2016 (Applicant/Inventor—Blizzard, et al.) (5 pages).
Response to Final Office Action dated Nov. 3, 2016 for U.S. Appl. No. 13/594,282, filed Aug. 24, 2012 now U.S. Pat. No. 9,314,407 on Apr. 19, 2016 (Applicant/Inventor—Blizzard, et al.) (11 pages).
Advisory Action dated Nov. 26, 2015 for U.S. Appl. No. 13/594,282, filed Aug. 24, 2012 now U.S. Pat. No. 9,314,407 on Apr. 19, 2016 (Applicant/Inventor—Blizzard, et al.) (2 pages).
Supplemental Response to Final Office Action dated Jan. 6, 2016 for U.S. Appl. No. 13/594,282, filed Aug. 24, 2012 now U.S. Pat. No. 9,314,407 on Apr. 19, 2016 (Applicant/Inventor—Blizzard, et al.) (11 pages).
Notice of Allowance dated Feb. 26, 2016 for U.S. Appl. No. 13/594,282, filed Aug. 24, 2012 now U.S. Pat. No. 9,314,407 on Apr. 19, 2016 (Applicant/Inventor—Blizzard, et al.) (6 pages).
STIC Prior Art Search submitted with the Non-Final Office Action dated Apr. 6, 2015 for U.S. Appl. No. 13/594,282, filed Aug. 24, 2012 now U.S. Pat. No. 9,314,407 on Apr. 19, 2016 (Applicant/Inventor—Blizzard, et al.) (147 pages).
U.S. Appl. No. 62/060,759, filed Oct. 7, 2014, Prusty (Kimmerling Holding, Group, LLC).
Chemical Abstract Compound, STN Express, RN 1566651-74-8, Mar. 11, 2014 (2 pages).
International Search Report and Written Opinion dated Jun. 30, 2016 for application PCT/US2015/054421, filed on Oct. 7, 2015 and published as WO 2016/057630 on Apr. 14, 2016 (Applicant—Kimmerling Holdings Group, LLC // Inventor—Prusty, et al.) (14 pages).
U.S. Appl. No. 61/527,231, filed Aug. 25, 2011, Blizzard
U.S. Appl. No. 61/548,091, filed Oct. 17, 2011, Blizzard
U.S. Appl. No. 61/553,396, filed Oct. 31, 2011, Blizzard.
U.S. Appl. No. 61/579,464, filed Dec. 22, 2011, Blizzard.
U.S. Appl. No. 61/608,882, filed Mar. 9, 2012, Blizzard.
U.S. Appl. No. 61/635,047, filed Apr. 18, 2012, Blizzard.
U.S. Appl. No. 13/594,282 (U.S. Pat. No. 9,314,407), filed Aug. 24, 2012 (Apr. 19, 2016), Blizzard.

* cited by examiner

TWO- AND THREE-COMPONENT SILOXANE AND RELATED COMPOUNDS AND COMPOSITIONS

CROSS REFERENCE TO RELATED APPLICATIONS

This application is a continuation application of U.S. application Ser. No. 13/594,282 filed Aug. 24, 2012, currently pending, which claims the benefit of:
U.S. Application No. 61/527,231 filed Aug. 25, 2011;
U.S. Application No. 61/548,091 filed Oct. 17, 2011;
U.S. Application No. 61/553,396 filed Oct. 31, 2011;
U.S. Application No. 61/579,464 filed Dec. 22, 2011;
U.S. Application No. 61/608,882 filed Mar. 9, 2012; and
U.S. Application No. 61/635,047 filed Apr. 18, 2012;
the entire disclosures of which are incorporated herein by reference.

FIELD OF THE INVENTION

The present invention generally relates to antimicrobial compositions. More particularly, it relates, inter alia, to antimicrobial compositions, some of which are curable, that are useful in dental, medical, and industrial applications for reinforcement and/or adhering two surfaces together.

BACKGROUND OF THE INVENTION

The field of dentistry has a large publication base dealing with compositions and materials for carrying out many necessary restructuring of teeth. One of the divisions of this field is in the use of adhesive materials to adhere dental structures and such materials are manufactured from acrylate chemistries.

Areas of use include cavity liners, filling materials to form composites, resin modified glass ionomers, temporary filling material, and the like.

The performance and service life of glass or ceramic filled polymeric composites in dentistry depends on the nature of the resin, the type and size of filler and interfacial phases, as well as the efficacy of the polymerization process used for curing in place.

The synergy that exists between the organic polymer matrix and the fillers is principally mediated by the interfacial interphasial phases of the mix. This latter phase develops as a result of the dual reactivity of silane coupling agents such as $XRSi(Z)_3$, a tri alkoxy functional molecule capable of reacting with the silanol groups of glass or ceramic fillers, upon hydrolysis of the alkoxy groups of the silane to form silanols and —Si—O—Si— bonds to filler surfaces, and also with the resin phase by graft copolymerization via the functional group, usually a methacrylic or vinyl group.

Thus, silanes per se are well-known in dentistry for bonding and adhesion. The chemistry of organofunctional silanes can be quite complex, involving hydrolytically initiated self-condensation reactions with or without solvents that culminate in polymeric silsesquioxane structures. This can also involve exchange reactions with hydroxylated or carboxylated monomers to form silyl ethers and esters, as well as the formation of silane derived interfaces, by adhesive coupling with siliceous mineral surfaces.

Most all of dental restoratives are multiphase materials having a composite microstructure involving one or more interfaces or interphases. With regard to composites, the term interface is reserved for the relatively sharp boundary layer that exists between the continuous or matrix phase and the dispersed or filler phase of these heterogeneous materials. In many composites, however, the microstructure is characterized by a broad, more gradient like transition zone that forms between the continuous and dispersed phases that is more accurately referred to as an interphase. For example, this diffuse type of interphase is characteristic of acid-base type dental cements, e.g. carboxylate and glass-ionomer cements, especially the latter. The sharp type of interface is more characteristic of amalgams and resin-base, macro-sized glass or ceramic filled composites.

Aspects of the instant invention is based on reactive silicates that can replace the current prior art silane and/or acrylate, glass ionomer, chemistries, or they can be used with such acrylate and glass ionomer chemistries to provide superior materials for adhesion and composite materials. The compositions and methods of the present invention are directed toward these, as well as other, important ends.

SUMMARY OF THE INVENTION

Accordingly, in a first embodiment, the invention is directed to compositions, comprising:
at least one compound of formula IV:

$$YO-\left(\begin{array}{c}OB\\|\\D\\|\\OA\end{array}\right)_p-OZ \qquad IV$$

wherein:
p is 1 to about 5;
D is independently Si, Ti, Al, or Zr;
A, B, Y, and Z are each independently selected from the group consisting of H, $C_1$-$C_8$alkyl, trifluoro-substituted $(C_1$-$C_8)$alkyl,

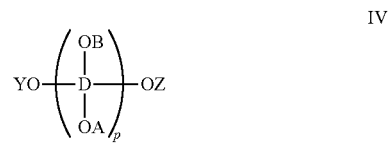

E is independently Si or Ti;
$R^a$ is independently a functional group comprising at least one curing group selected from the group consisting of acrylate, methacrylate, $(C_2$-$C_8)$ alkenyl, glycidyloxy, ester, amino, acrylamide, methacrylamide, isocyanato, amino acid, nucleic acid, and mercapto$(C_1$-$C_6)$alkyl;
$R^b$ is independently

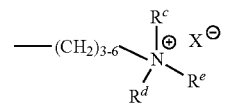

wherein:
$R^c$ is $(C_1$-$C_2)$alkyl;
$R^d$ is $(C_1$-$C_2)$alkyl or phenyl;
$R^e$ is $(C_6$-$C_{22})$alkyl;
$X^-$ is an anion selected from the group consisting of chloride, bromide, fluoride, iodide, sulfonate, and acetate;

each $R^y$ is, independently, H, $(C_1-C_8)$alkyl, or trifluoro-substituted $(C_1-C_8)$alkyl; and wherein at least one of A, B, Y, and Z is

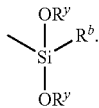

In another embodiment, the compositions further comprise:
at least one filler;
wherein said one compound of formula IV is sorbed on said filler.

In other embodiments, the compositions further comprise:
Portland cement.

In yet other embodiments, the compositions, further comprise:
cement, comprising:
about 50% by weight to about 70% by weight, based on the total weight of cement, of calcia;
about 15% by weight to about 29% by weight, based on the total weight of cement, of silica;
less than about 0.5% by weight, based on the total weight of cement, of iron oxide; and
optional radiopacifier.

In other embodiments, the compositions, further comprise:
at least one natural rubber, synthetic rubber, or a combination thereof.

In another embodiment, the compositions, further comprise:
at least one first polymer selected from the group consisting of thermoplastic polymer, thermosetting polymer, and mixtures thereof.

In yet other embodiments, the invention is directed to polymeric articles, comprising:
said compositions described herein or a polymerized residue of said compositions described herein.

In further embodiments, the invention is directed to coating materials, comprising:
said compositions described herein.

In other embodiments, the invention is directed to compositions comprising:
the polymerized residue of said compositions described herein.

In another embodiment, the invention is directed to toothpastes, comprising:
said compositions described herein.

In other embodiments, the invention is directed to mouthwashes, comprising:
said compositions described herein.

In yet other embodiments, the invention is directed to contact lenses, comprising:
said compositions described herein or a polymerized residue of said compositions described herein.

In yet other embodiments, the invention is directed to electronic components, comprising:
a polymerized residue of said compositions described herein, especially where the curing functionality is epoxy.

In alternate embodiments, the invention is directed to processes of preparing a polymer, comprising:
providing at least one composition comprising the compound of formula IV;

substantially fully hydrolyzing said compound of formula IV to form a substantially fully hydrolyzed compound of formula IV; and
reacting said substantially fully hydrolyzed compound of formula IV with at least one co-monomer.

In other embodiments, the invention is directed to the products produced by the processes and methods described herein.

In yet other embodiments, the invention is directed to processes of preparing a compound of formula IV:

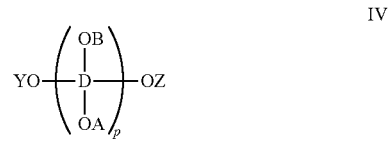

wherein:
p is 1 to about 5;
D is independently Si, Ti, Al, or Zr;
A, B, Y, and Z are each independently selected from the group consisting of H, $(C_1-C_8)$alkyl, or trifluoro-substituted $(C_1-C_8)$alkyl,

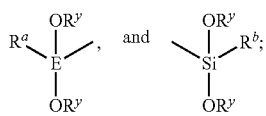

E is independently Si or Ti;
$R^a$ is independently a functional group comprising at least one curing group selected from the group consisting of acrylate, methacrylate, $(C_2-C_8)$ alkenyl, glycidyloxy, ester, amino, acrylamide, methacrylamide, isocyanato, amino acid, nucleic acid, and mercapto$(C_1-C_8)$alkyl;
$R^b$ is independently

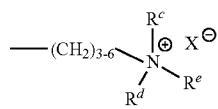

wherein:
$R^c$ is $(C_1-C_2)$alkyl;
$R^d$ is $(C_1-C_2)$alkyl or phenyl;
$R^e$ is $(C_6-C_2)$alkyl;
$X^-$ is an anion selected from the group consisting of chloride, bromide, fluoride, iodide, sulfonate, and acetate;
each $R^y$ is, independently, H, $(C_1-C_8)$alkyl, or trifluoro-substituted $(C_1-C_8)$alkyl; and
wherein at least one of A, B, Y, and Z is

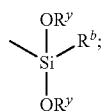

said process, comprising the step(s) of:
preparing a mixture comprising:

a. 

$\{D(OR^g)_4\}_y,$ b. 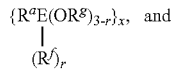

$\{R^aE(OR^g)_{3-r}\}_x,$ and
$\quad\quad |$
$\quad\quad (R^f)_r$ c. 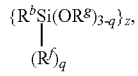

$\{R^bSi(OR^g)_{3-q}\}_z,$
$\quad |$
$\quad (R^f)_q$ wherein:
$R^f$ is independently is hydroxyl, $(C_1\text{-}C_8)$alkyl, or substituted $(C_1\text{-}C_8)$alkyl;
each $R^g$ is, independently, H, $(C_1\text{-}C_8)$alkyl, trifluoro-substituted $(C_1\text{-}C_8)$alkyl, $CH_3\text{---}C(\!=\!O)\text{---}O\text{---}$, or oxime radical;
the molar ratio of x:y:z is 1-3:4:1-3;
q and r each independently have a value of 2 or less; and
adding a substantially stoichiometric amount of water and at least one catalyst to said mixture for hydrolysis and condensation.

In another embodiment, the invention is directed to kits, comprising:
a composition described herein;
at least one polymerization initiator;
optionally, at least one synergist;
optionally, at least one filler; and
optionally, at least one co-monomer.

In other embodiments, the invention is directed to compositions, comprising:
at least one filler;
at least one compound of formula X:

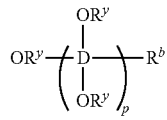

X wherein:
p is 1 to about 5;
D is independently Ti, Al, or Zr;
$R^b$ is independently

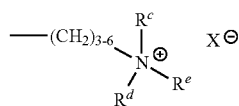

wherein:
$R^c$ is $(C_1\text{-}C_2)$alkyl;
$R^d$ is $(C_1\text{-}C_2)$alkyl or phenyl;
R is $(C_6\text{-}C_{22})$alkyl;
$X^-$ is an anion selected from the group consisting of chloride, bromide, fluoride, iodide, sulfonate, and acetate;

each $R^y$ is, independently, H, $(C_1\text{-}C_4)$alkyl, or trifluoro-substituted $(C_1\text{-}C_4)$alkyl; and
wherein said one compound of formula X is sorbed on said filler.

In yet other embodiments, the invention is directed to compositions, comprising:
at least one compound of formula IV:

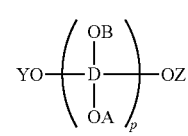

IV wherein:
p is 1 to about 5;
D is independently Si, Ti, Al, or Zr;
A, B, Y, and Z are each independently selected from the group consisting of H, $(C_1\text{-}C_8)$alkyl, or trifluoro-substituted $(C_1\text{-}C_8)$alkyl,

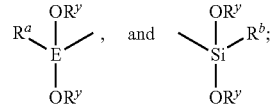

E is independently Si or Ti;
$R^a$ is independently a functional group comprising at least one curing group selected from the group consisting of acrylate, methacrylate, $(C_2\text{-}C_8)$ alkenyl, glycidyloxy, ester, amino, acrylamide, methacrylamide, isocyanato, amino acid, nucleic acid, and mercapto$(C_1\text{-}C_8)$alkyl;
each $R^y$ is, independently, H, $(C_1\text{-}C_4)$alkyl, trifluoro-substituted $(C_1\text{-}C_4)$alkyl; and
wherein at least one of A, B, Y, and Z is

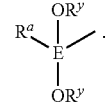

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
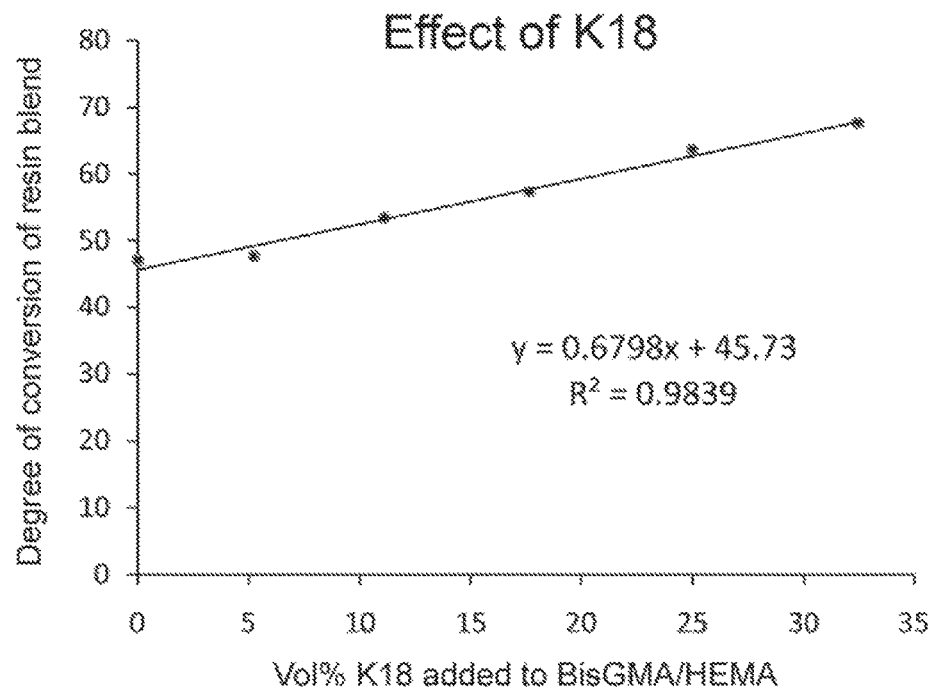
FIG. 1 is a plot of the effect of addition of different concentrations of Sample 26 on the degree of conversion of a hydrophilic resin blend consisting of BisGMA-HEMA.

As employed above and throughout the disclosure, the following terms, unless otherwise indicated, shall be understood to have the following meanings.

As used herein, the singular forms "a," "an," and "the" include the plural reference unless the context clearly indicates otherwise.

"Alkyl," as used herein, refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms or 1 to 6 carbon atoms (C.sub.1-C.sub.6) being preferred, and with from about 1 to about 4 carbon atoms. Alkyl groups include, but are not limited to, methyl, ethyl, n-propyl, isopropyl, n-butyl, isobutyl, t-butyl, n-pentyl, cyclopentyl, cyclopropyl, isopentyl, neopentyl, n-hexyl, isohexyl, cyclohexyl, cyclooctyl, adamantyl, 3-methylpentyl, 2,2-dimethylbutyl, and 2,3-dimethylbutyl. A branched alkyl group has at least 3 carbon atoms (e.g., an isopropyl group), and in various embodiments, has up to 6 carbon atoms, i.e., a branched lower alkyl group. A branched alkyl group has at least 3 carbon atoms (e.g., an isopropyl group), and in various embodiments, has up to 6 carbon atoms, i.e., a branched lower alkyl group.

"Alkenyl," as used herein, refers to an optionally substituted, singly unsaturated, straight, branched, or cyclic hydrocarbon having from about 2 to about 20 carbon atoms (and all combinations and subcombinations of ranges and specific numbers of carbon atoms therein), with from about 2 to about 8 carbon atoms or 2 to 6 carbon atoms ($C_2$-$C_6$) being preferred. Alkenyl groups include, but are not limited to, ethenyl (or vinyl), allyl, propenyl, butenyl, pentenyl, cyclopentenyl, hexenyl, and octenyl.

"Alkylenyl," as used herein, refer to the subsets of alkyl groups, as defined herein, including the same residues as alkyl but having two points of attachment within a chemical structure. Examples of ($C_1$-$C_6$)alkylenyl include methylenyl (—$CH_2$—), ethylenyl (—$CH_2CH_2$—), propylenyl (—$CH_2CH_2CH_2$—), and dimethylpropylenyl (—$CH_2C(CH_3)_2CH_2$—).

"Aryl," as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons ($C_6$-$C_{10}$) being preferred. Non-limiting examples include, for example, phenyl, naphthyl, anthracenyl, and phenanthrenyl.

As used herein, the terms "optionally substituted" or "substituted or unsubstituted" are intended to refer to the optional replacement of up to four hydrogen atoms with up to four independently selected substituent groups as defined herein. Unless otherwise specified, suitable substituent groups independently include hydroxyl, nitro, amino, imino, cyano, halo, thio, sulfonyl, aminocarbonyl, carbonylamino, carbonyl, oxo, guanidine, carboxyl, formyl, alkyl, perfluoroalkyl, alkylamino, dialkylamino, alkoxy, alkoxyalkyl, alkylcarbonyl, arylcarbonyl, alkylthio, aryl, heteroaryl, a heterocyclic ring, cycloalkyl, hydroxyalkyl, carboxyalkyl, haloalkyl, alkenyl, alkynyl, arylalkyl, aryloxy, heteroaryloxy, heteroarylalkyl, and the like. Substituent groups that have one or more available hydrogen atoms can in turn optionally bear further independently selected substituents, to a maximum of three levels of substitutions. For example, the term "optionally substituted alkyl" is intended to mean an alkyl group that can optionally have up to four of its hydrogen atoms replaced with substituent groups as defined above (i.e., a first level of substitution), wherein each of the substituent groups attached to the alkyl group can optionally have up to four of its hydrogen atoms replaced by substituent groups as defined above (i.e., a second level of substitution), and each of the substituent groups of the second level of substitution can optionally have up to four of its hydrogen atoms replaced by substituent groups as defined above (i.e., a third level of substitution).

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

As used herein, the phrase "substantially" means have no more than about 10% difference between the target and actual level, preferably less than about 5% difference, more preferably, less than about 1% difference.

The materials of this invention are new and novel materials that have been found to provide adhesion on many varied surfaces. By careful, controlled hydrolysis of the precursor monomers, one can obtain these materials at very low molecular weights, the detail of which can be found infra in the specification, and in the examples.

Accordingly, in a first embodiment, the invention is directed to compositions, comprising:

at least one compound of formula IV:

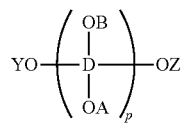

wherein:
p is 1 to about 5;
D is independently Si, Ti, Al, or Zr;
A, B, Y, and Z are each independently selected from the group consisting of H, $C_1$-$C_8$alkyl, trifluoro-substituted ($C_1$-$C_8$)alkyl,

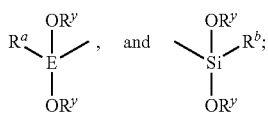

E is independently Si or Ti;
$R^a$ is independently a functional group comprising at least one curing group selected from the group consisting of acrylate, methacrylate, ($C_2$-$C_8$) alkenyl, glycidyloxy, ester, amino, acrylamide, methacrylamide, isocyanato, amino acid, nucleic acid, and mercapto($C_1$-$C_6$)alkyl;
$R^b$ is independently

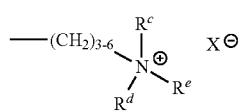

wherein:
$R^c$ is ($C_1$-$C_2$)alkyl;
$R^d$ is ($C_1$-$C_2$)alkyl or phenyl;
$R^e$ is ($C_6$-$C_{22}$)alkyl;
$X^-$ is an anion selected from the group consisting of chloride, bromide, fluoride, iodide, sulfonate, and acetate;

each $R^y$ is, independently, H, ($C_1$-$C_8$)alkyl, or trifluoro-substituted ($C_1$-$C_8$)alkyl; and
wherein at least one of A, B, Y, and Z is

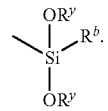

Preferably in certain embodiments of compounds of formula I, III, IV, V, or X, at least one of A, B, Y, and Z is

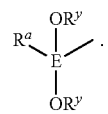

Preferably in certain embodiments of compounds of formula I, III, IV, V, or X, A, B, Y, and Z are each independently selected from the group consisting of H,

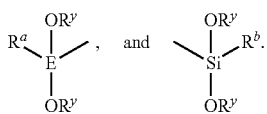

Preferably in certain embodiments of compounds of formula I, III, IV, V, or X, $R^a$ is acrylate, methacrylate, or vinyl.

Preferably in certain embodiments of compounds of formula I, III, IV, V, or X, $R^y$ is H or ($C_1$-$C_2$)alkyl. Ethyl is preferred for certain dental and medical applications. In certain embodiments $R^y$ is H.

Preferably in certain embodiments of compounds of formula I, III, IV, V, or X, $R^b$ is independently —($C_3$-$C_6$ alkylenyl)-(dimethyl)-($C_6$-$C_{22}$alkyl) quaternary ammonium chloride or —($C_3$-$C_6$ alkylenyl)-(methyl)-(phenyl)-($C_6$-$C_{22}$alkyl) quaternary ammonium chloride. In certain embodiments, $R^b$ is —($C_3$-$C_6$)alkylenyl-dimethyl-($C_{18}$alkyl) quaternary ammonium chloride, especially $R^b$ is —($C_3$ alkylenyl)-(dimethyl)-($C_{18}$alkyl) quaternary ammonium chloride, such Aegis 5700 or 5772 commercially available from Aegis or $R^b$ is —($C_3$-$C_6$)alkylenyl-methyl-phenyl-($C_6$-$C_{22}$alkyl) quaternary ammonium chloride, which may be prepared by N-alkylation of N-hexylaniline in a two-step process where N-hexylanlysis is reacted with 3-chloropropyl)triethoxysilane to yield a tertiary amine which then is further quarternized in the second step by reacting with iodomethane, such as described in Saif, et al., *Langmuir*, 2009, 25, 377-379.

In another embodiment, the compositions further comprise:
at least one filler;
wherein said one compound of formula IV is sorbed on said filler.

In other embodiments, the compositions further comprise:
Portland cement.

In yet other embodiments, the compositions, further comprise:
cement, comprising:
about 50% by weight to about 70% by weight, based on the total weight of cement, of calcia;

about 15% by weight to about 29% by weight, based on the total weight of cement, of silica;

less than about 0.5% by weight, based on the total weight of cement, of iron oxide; and optional radiopacifier.

In other embodiments, the compositions, further comprise:

at least one natural rubber, synthetic rubber, or a combination thereof.

In another embodiment, the compositions, further comprise:

at least one first polymer selected from the group consisting of thermoplastic polymer, thermosetting polymer, and mixtures thereof.

In yet other embodiments, the invention is directed to polymeric articles, comprising:

said compositions described herein or a polymerized residue of said compositions described herein.

In further embodiments, the invention is directed to coating materials, comprising:

said compositions described herein.

In other embodiments, the invention is directed to compositions comprising:

the polymerized residue of said compositions described herein.

In another embodiment, the invention is directed to toothpastes, comprising:

said compositions described herein.

In other embodiments, the invention is directed to mouthwashes, comprising:

said compositions described herein.

In yet other embodiments, the invention is directed to contact lenses, comprising:

said compositions described herein or a polymerized residue of said compositions described herein.

In alternate embodiments, the invention is directed to processes of preparing a polymer, comprising:

providing at least one composition comprising the compound of formula IV;

substantially fully hydrolyzing said compound of formula IV to form a substantially fully hydrolyzed compound of formula IV; and reacting said substantially fully hydrolyzed compound of formula IV with at least one co-monomer.

In other embodiments, the invention is directed to the products produced by the processes and methods described herein.

In yet other embodiments, the invention is directed to processes of preparing a compound of formula IV:

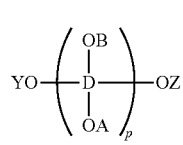

wherein:
p is 1 to about 5;
D is independently Si, Ti, Al, or Zr;
A, B, Y, and Z are each independently selected from the group consisting of H, (C$_1$-C$_8$)alkyl, or trifluoro-substituted (C$_1$-C$_8$)alkyl,

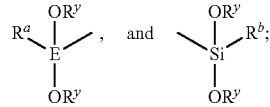

E is independently Si or Ti;
R$^a$ is independently a functional group comprising at least one curing group selected from the group consisting of acrylate, methacrylate, (C$_2$-C$_8$) alkenyl, glycidyloxy, ester, amino, acrylamide, methacrylamide, isocyanato, amino acid, nucleic acid, and mercapto(C$_1$-C$_8$)alkyl;
R$^b$ is independently

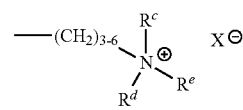

wherein:
R$^c$ is (C$_1$-C$_2$)alkyl;
R$^d$ is (C$_1$-C$_2$)alkyl or phenyl;
R$^e$ is (C$_6$-C$_{22}$)alkyl;
X$^-$ is an anion selected from the group consisting of chloride, bromide, fluoride, iodide, sulfonate, and acetate;
each R$^y$ is, independently, H, (C$_1$-C$_8$)alkyl, or trifluoro-substituted (C$_1$-C$_8$)alkyl; and
wherein at least one of A, B, Y, and Z is

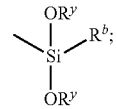

said process, comprising the step(s) of:
preparing a mixture comprising:

a.

$\{D(OR^g)_4\}_y$, b.

$\{R^aE(OR^g)_{3-r}\}_x$, and
$|$
$(R^f)_r$ c.

$\{R^bSi(OR^g)_{3-q}\}_z$,
$|$
$(R^f)_q$ wherein:
R$^f$ is independently is hydroxyl, (C$_1$-C$_8$)alkyl, or substituted (C$_1$-C$_8$)alkyl;
each R$^g$ is, independently, H, (C$_1$-C$_8$)alkyl, trifluoro-substituted (C$_1$-C$_8$)alkyl, CH$_3$—C(=O)—O—, or oxime radical;
the molar ratio of x:y:z is 1-3:4:1-3;
q and r each independently have a value of 2 or less; and
adding a substantially stoichiometric amount of water and at least one catalyst to said mixture for hydrolysis and condensation.

In another embodiment, the invention is directed to kits, comprising:
a composition described herein;
at least one polymerization initiator (such as a photoinitiator);
optionally, at least one synergist (such as, for example, ethyl-4-(N,N'-dimethylaminobenzoate);
optionally, at least one filler; and
optionally, at least one co-monomer (such as, for example, ethylene, propylene, vinyl chloride, acrylate, methacrylate, and combinations thereof).

In other embodiments, the invention is directed to compositions, comprising:
at least one filler;
at least one compound of formula X:

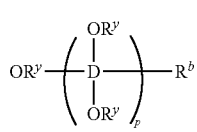

wherein:
p is 1 to about 5;
D is independently Ti, Al, or Zr;
$R^b$ is independently

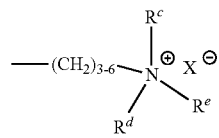

wherein:
$R^c$ is $(C_1-C_2)$alkyl;
$R^d$ is $(C_1-C_2)$alkyl or phenyl;
$R^e$ is $(C_6-C_{22})$alkyl;
$X^-$ is an anion selected from the group consisting of chloride, bromide, fluoride, iodide, sulfonate, and acetate;
each $R^y$ is, independently, H, $(C_1-C_4)$alkyl, or trifluoro-substituted $(C_1-C_4)$alky; and
wherein said one compound of formula X is sorbed on said filler.

In yet other embodiments, the invention is directed to compositions, comprising:
at least one compound of formula IV:

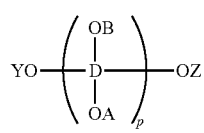

wherein:
p is 1 to about 5;
D is independently Si, Ti, Al, or Zr;
A, B, Y, and Z are each independently selected from the group consisting of H, $C_1-C_4$alkyl, and

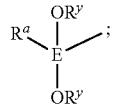

E is independently Si or Ti;
$R^a$ is independently a functional group comprising at least one curing group selected from the group consisting of acrylate, methacrylate, $(C_2-C_8)$ alkenyl, glycidyloxy, ester, amino, acrylamide, methacrylamide, isocyanato, amino acid, nucleic acid, and mercapto$(C_1-C_8)$alkyl;
each $R^y$ is, independently, H, $(C_1-C_4)$alkyl, trifluoro-substituted $(C_1-C_4)$alkyl; and
wherein at least one of A, B, Y, and Z is

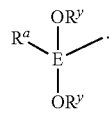

Another embodiment of this invention is a water solution of the compositions described herein.

Still another embodiment of this invention is a water-alcohol solution of the compositions described herein.

Yet another embodiment is the use of the material described herein as an adhesive (primer) and the use of the material described herein in commercial adhesives used in dentistry.

Still another embodiment is the use of a material described herein as an additive to dental compositions for adhesion of the dental composition to a tooth.

In addition, the materials of this invention can act as tooth desensitizers when placed on a tooth, and still further, this material can be added to filler material for teeth, especially filling materials such as siloxanes, glass ionomers, methacrylates, and silver amalgams.

In still other embodiments, the materials of the invention may be used in contact lenses as the primary material or as a secondary material.

In other embodiments, the invention is directed to compounds of formula III:

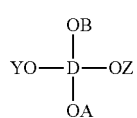

wherein:
D is Si, Ti, Al, or Zr;
A, B, Y, and Z are each independently selected group consisting of H, $C_1-C_4$alkyl,

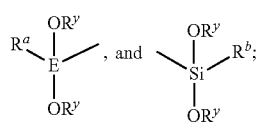

E is Si or Ti;
$R^a$ is a curing group selected from acrylate, methacrylate, vinyl, glycidyloxy, epoxy, ester, and isocyanate;

$R^b$ is independently —$(C_3-C_6)$alkylenyl-dimethyl-$(C_6-C_{22}$alkyl) quaternary ammonium chloride or —$(C_3-C_6)$alkylenyl-methyl-phenyl-$(C_6-C_{22}$alkyl) quaternary ammonium chloride;

each $R^y$ is, independently, H or $C_1-C_4$alkyl;

wherein at least one of A, B, Y, and Z is

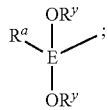

and wherein at least one of A, B, Y, and Z is

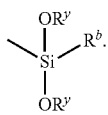

In further embodiments, the invention is directed to compositions, comprising:

a compound of formula I, III, IV, V, or X;

Portland cement; and optional radiopacifier.

In other embodiment, the invention is directed to compositions, comprising:

a compound of formula I, III, IV, V, or X; and cement, comprising:

about 50% by weight to about 70% by weight, based on the total weight of cement, of calcia;

about 15% by weight to about 29% by weight, based on the total weight of cement, of silica;

less than about 0.5% by weight, based on the total weight of cement, of iron oxide; and optional radiopacifier.

In other embodiment, the invention is directed to compositions, comprising:

at least one filler; and at least one compound selected from the group of formula IV and formula V:

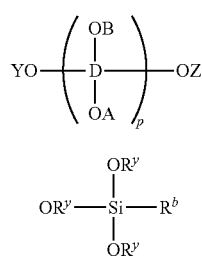

(covers 2- and 3-component) (covers 1-component)

wherein:

p is 1 to about 5;

D is Si, Ti, Al, or Zr;

A, B, Y, and Z are each independently selected group consisting of H, $C_1-C_4$alkyl,

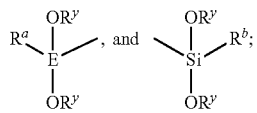

E is Si or Ti;

$R^a$ is a curing group selected from acrylate, methacrylate, vinyl, glycidyloxy, epoxy, ester, and isocyanate;

$R^b$ is independently —$(C_3-C_6)$alkylenyl-dimethyl-$(C_6-C_{22}$alkyl) quaternary ammonium chloride or —$(C_3-C_6)$alkylenyl-methyl-phenyl-$(C_6-C_{22}$alkyl) quaternary ammonium chloride;

each R is, independently, H or $C_1-C_4$alkyl; and wherein at least one of A, B, Y, and Z is

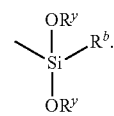

In other embodiment, the invention is directed to compositions, comprising:

at least one compound selected from the group of formula IV and formula V:

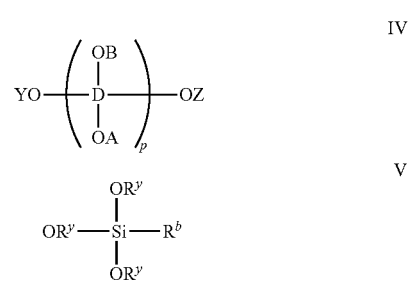

(covers 2- and 3-component) (covers 1-component)

wherein:

p is 1 to about 5;

D is Si, Ti, Al, or Zr;

A, B, Y, and Z are each independently selected group consisting of H, $C_1-C_4$alkyl,

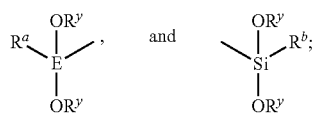

E is Si or Ti;

$R^a$ is a curing group selected from acrylate, methacrylate, vinyl, glycidyloxy, epoxy, ester, and isocyanate;

$R^b$ is independently —$(C_3-C_6)$alkylenyl-dimethyl-$(C_6-C_{22}$alkyl) quaternary ammonium chloride or —$(C_3-C_6)$alkylenyl-methyl-phenyl-$(C_6-C_{22}$alkyl) quaternary ammonium chloride;

each R is, independently, H or $C_1-C_4$alkyl; and wherein at least one of A, B, Y, and Z is

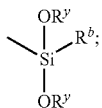

and optionally, at least one filler;
wherein said compound of formula IV or formula V is sorbed on said filler.

In certain embodiments, the compositions of the invention further comprise at least one natural rubber, synthetic rubber, or a combination thereof. In certain other embodiments, the compositions of the invention further comprise at least one first polymer selected from the group consisting of thermoplastic polymer, thermosetting polymer, and mixtures thereof. In certain embodiments, the compositions of the invention may be in the form of a powder or a master batch.

In other embodiment, the invention is directed to methods of preparing a polymer, comprising:

providing at least one composition comprising the compound of formula IV, described herein;

hydrolyzing said compound of formula IV to form a hydrolyzed compound of formula IV; and reacting said hydrolyzed compound of formula IV with at least one co-monomer.

In certain embodiments, the materials have the average general formula

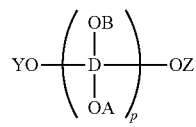

IV which is derived by the hydrolysis of the precursors

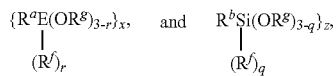

wherein:
$R^f$ is independently is hydroxyl, $(C_1-C_8)$alkyl, or substituted $(C_1-C_8)$alkyl;
each $R^g$ is, independently, H, $(C_1-C_8)$alkyl, trifluoro-substituted $(C_1-C_8)$alkyl, $CH_3-C(=O)-O-$, or oxime radical;
the molar ratio of x:y:z is 1-3:4:1-3; and
q and r each independently have a value of 2 or less;
in conjunction with the orthosilicate, or orthotitanate, or orthozirconate having the general formula $\{D(OR_g)_4\}_y$, wherein the molar ratio of x:y:z is 0.25-3:4:0.25-3.

This hydrolysis is carried out using a stoichiometric or substantially stoichiometric amounts of water and a catalyst for hydrolysis and condensation. Stoichiometric amounts of water, or, an amount of water greater than stoichiometric, result in low molecular weight materials, which is one of the objectives of the method in this invention. Caution should be noted for the use of substantially lesser amounts of water as that will result in a residual amount of alkoxy in the material which is undesirable for purposes of this invention.

An example of an acrylate starting material is $(CH_3O)_3Si(CH_2)_3OOC(CH_3)C=CH_2$ and an example of a starting material for epoxy is 3-glycidoxypropyltrimethoxysilane. The molecule vinylSi$(OCH_3)_3$ is an excellent starting material for supplying a vinyl functionality which can be used with addition reactions, polymerization, free radical reactions and the like to provide a cure mechanism. In addition, a molecule such as allylSi$(OCH_3)_3$ can be used to provide an unsaturated cure mechanism. Still further, the molecule $CH_2=CHCH_2CH_2CH_2CH_2CH_2CH_2Si(OCH_3)_3$ can be used to provide the octene wherein the octene is another unsaturated cure mechanism. It is believed by the inventors herein that any alkene group of from 2 to 8 carbons long will provide such a cure mechanism. $(CH_3O)_3Si(CH_2)_3NCO$ can be used to furnish the isocyanato functionality for cure, while $(CH_3O)_3SiCH_2$ester can be used to supply the ester functionality for cure.

It should be noted that the above-mentioned silanes can be dialkoxysilanes, such as $(CH_3)(vinyl)Si(CH_3O)_2$ to provide substituents other than the cure functionalities. Such materials allow one to obtain more hydrophobicity, for example, when the molecule has a structure such as $(CF_3CH_2CH_2)(vinyl)Si(CH_3O)_2$ or perfluorinated silanes such as $(CF_3CF_2CH_2)(vinyl)Si(CH_3O)_2$. Also, the silanes can be monoalkoxysilanes such as $(CH_3)_2(vinyl)Si(CH_3O)$ or $(CF_3CH_2CH_2)(CH_3)(vinyl)Si(CH_3O)$.

A second part of the inventive molecules of this invention is provided by the precursor silane

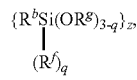

wherein:
$R^b$ group is independently

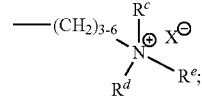

$R^c$ is $(C_1-C_2)$alkyl;
$R^d$ is $(C_1-C_2)$alkyl or phenyl;
$R^e$ is $(C_6-C_{22})$alkyl;
$X^-$ is an anion selected from the group consisting of chloride, bromide, fluoride, iodide, sulfonate, and acetate;
each $R^y$ is, independently, H, $(C_1-C_4)$alkyl, or trifluoro-substituted $(C_1-C_4)$alkyl.

Preferred for this invention is the silane:

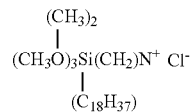

It is believed by the inventors herein that the key to this invention is the use of the molecule: $\{D(OR^g)_4\}_y$ as the third component of this invention. D in the case of this invention is independently selected from the group consisting of Si, Ti, Al, and Zr. Preferred for this invention is Si and Ti and most preferred is Si.

The $(OR^g)$ group is selected from the group consisting of $-OCH_3$, $-OCH_2CH_3$, $-OCH(CH_3)_2$, $-O(CH_2)_2CH_3$, $-OCH_2CH(CH_3)_2$, $-O$(2-ethylhexyl), acetoxy, and, oximo. Preferred for this invention are the groups —OCH$_3$, —OCH$_2$CH$_3$, and —OCH(CH$_3$)$_2$, and most preferred are the —OCH$_3$ and —OCH$_2$CH$_3$ groups. Preferred orthosilicates and orthotitanates for this invention are Si(OCH$_2$CH$_3$)$_4$ and Ti(—OCH(CH$_3$)$_2$)$_4$.

The method that is utilized for the preparation of the materials of this invention comprises providing the components:

a.
$$\{W(OR''')_4\}_y,$$

b.
$$\{RSi(OR''')_{3-p}\}_x, \text{ and}$$
$$|$$
$$(R'''')_p$$

c.
$$\{R'Si(OR''')_{3-q}\}_z,$$
$$|$$
$$(R'''')_q$$

wherein the molar ratio of x:y:z is 0.25-3:4:0.25-3, p and q each independently have a value of 2 or less, and co-hydrolyzing the components in the presence of a stoichiometric amount of water, and a catalyst for hydrolysis and condensation.

Stoichiometry is based on the number of hydrolysable groups on the combined components. The reaction is carried out in the presence of base or acid, with acid being the preferred catalyst. The acid catalysts are preferred to be HCl, phosphoric, and acetic acids, with HCl and phosphoric acids being most preferred.

Bases that are useable herein are amines, NaOH, KOH and the like and preferred for this invention is NaOH. The hydrolysis reaction is carried out by combining the components in a predetermined ratio and then adding acidic or basic water to the components at a controlled rate to form silanols from the alkoxy moieties. For some end use applications of the inventive materials, a slightly higher molecular weight (higher number of silanol reactive groups) is preferred and in this case, the silicate component is treated for a short period of time by acidic or basic water to cause the silicate component to hydrolyze and condense before the other components are added.

By the preferred means, the following reaction sequence is achieved using acrylate as the cure segment of the molecule:

(CH$_3$O)$_3$Si(CH$_2$)$_3$OOC(CH$_3$)C═CH$_2$ +

$$\begin{array}{c} (CH_3)_2 \\ | \\ (CH_3O)_3Si(CH_2)N^+ \; Cl^- \\ | \\ (C_{18}H_{37}) \end{array} + Si(OCH_2CH_3)_4 \xrightarrow[HCl]{water}$$

$$\begin{array}{c} \;\;\;\;\;\; OH\;OH\;OH \;\;\; (CH_3)_2 \\ \;\;\;\;\;\;\;\; | \;\;\; | \;\;\; | \;\;\;\;\;\;\; | \\ CH_2\!=\!C(CH_3)COO(CH_2)SiOSiOSi(CH_2)N^+ \; Cl^- \\ \;\;\;\;\;\;\;\; | \;\;\; | \;\;\; | \;\;\;\;\;\;\; | \\ \;\;\;\;\;\;\; OH\;OH\;OH \;\;\;\;\; (C_{18}H_{37}) \end{array}$$

No heat is used in this reaction as higher temperatures (in excess of about 150° C.) may result in a gelation of the reaction mixture. There is a small exotherm from the hydrolysis reaction but the heat is not sufficient to provide problems with the resultant product. No solvents are required in this reaction, but it is within the scope of this invention to utilize solvents. It should be noted that the byproduct of the hydrolysis reaction is alcohol. Typically, the products of this reaction do not need filtration.

As mentioned supra, it is possible to enhance the molecular weight and thereby increase the amount of silanol functionality on the molecule by first mildly hydrolyzing the ortho precursor and then adding the remainder of the components.

Thus, a molecule having the following average formula may be obtained:

$$\begin{array}{c} \;\;\;\;\;\; OH\;OH\;OH\;OH \;\;\; (CH_3)_2 \\ \;\;\;\;\;\;\;\; | \;\;\; | \;\;\; | \;\;\; | \;\;\;\;\;\;\; | \\ CH_2\!=\!C(CH_3)COO(CH_2)SiOSiOSiOSi(CH_2)N^+ \; Cl^- \\ \;\;\;\;\;\;\;\; | \;\;\; | \;\;\; | \;\;\; | \;\;\;\;\;\;\; | \\ \;\;\;\;\;\;\; OH\;OH\;OH\;OH \;\;\;\;\; (C_{18}H_{37}) \end{array}$$

or, one can provide a material having the formula:

$$\begin{array}{c} \;\;\;\;\;\; OH\;OH\;OH\;OH\;OH \;\;\; (CH_3)_2 \\ \;\;\;\;\;\;\;\; | \;\;\; | \;\;\; | \;\;\; | \;\;\; | \;\;\;\;\;\;\; | \\ CH_2\!=\!C(CH_3)COO(CH_2)SiOSiOSiOSiOSi(CH_2)N^+ \; Cl^- \\ \;\;\;\;\;\;\;\; | \;\;\; | \;\;\; | \;\;\; | \;\;\; | \;\;\;\;\;\;\; | \\ \;\;\;\;\;\;\; OH\;OH\;OH\;OH\;OH \;\;\;\;\; (C_{18}H_{37}) \end{array}$$

In other embodiments, a molecule may be obtained having the average formula $$\begin{array}{ccc} OH & OH & OH \\ | & | & | \\ (R^aSi)\!-\!(O\!-\!Si)_s\!-\!O\!-\!(SiR^b), \\ | & | & | \\ OH & OH & OH \end{array}$$

wherein s has an average value of from 1 to 5.

In other embodiments, a molecule may be obtained having the average formula $$\begin{array}{ccc} OH & RSiO & OH \\ | & | & | \\ (R^aSi)\!-\!(O\!-\!Si)_t\!-\!O\!-\!(SiR^b), \\ | & | & | \\ OH & OH & OH \end{array}$$

wherein t has an average value of from 1 to 5.

In other embodiments, a molecule may be obtained having the average formula $$\begin{array}{ccc} OH & RSiO & OH \\ | & | & | \\ (R^aSi)\!-\!(O\!-\!Si)_u\!-\!O\!-\!(SiR^b), \\ | & | & | \\ OH & RSiO & OH \end{array}$$

wherein u has an average value of from 1 to 5.

In other embodiments, a molecule may be obtained having the average formula

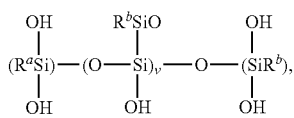

wherein v has an average value of from 1 to 5.

In other embodiments, a molecule may be obtained having the average formula

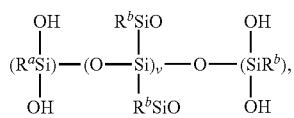

wherein w has an average value of from 1 to 5.

In other embodiments, a molecule may be obtained having the average formula

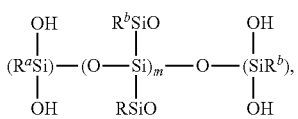

wherein m has an average value of from 1 to 5.

In other embodiments, a molecule may be obtained having the average formula

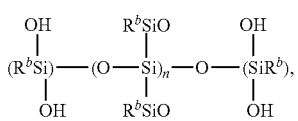

wherein n has an average value of from 1 to 5.

In other embodiments, the invention is directed to compounds of formula III:

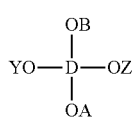

III wherein:

D is Si, Ti, Al. or Zr;

A, B, Y, and Z are each independently selected group consisting of H, $C_1$-$C_4$alkyl,

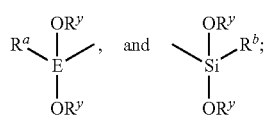

E is Si or Ti;

$R^a$ is a curing group selected from acrylate, methacrylate, vinyl, glycidyloxy, epoxy, ester, and isocyanate;

$R^b$ is independently —($C_3$-$C_6$)alkylenyl-dimethyl-($C_6$-$C_{22}$alkyl) quaternary ammonium chloride or —($C_3$-$C_6$)alkylenyl-methyl-phenyl-($C_6$-$C_{22}$alkyl) quaternary ammonium chloride;

each $R^y$ is, independently, H or $C_1$-$C_4$alkyl;

wherein at least one of A, B, Y, and Z is

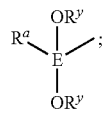

and wherein at least one of A, B, Y, and Z is

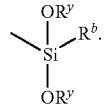

In other embodiments, a composition is provided, comprising the compound of formula I, III, IV, V, or X and a composite material.

In other embodiments, a composition is provided, comprising the compound of formula I, III, IV, V, or X and a modified glass ionomer.

In other embodiments, a composition is provided, comprising the compound of formula I, III, IV, V, or X and a zinc phosphate cement.

In other embodiments, a composition is provided, comprising the compound of formula I, III, IV, V, or X and a zinc oxide eugenol.

In other embodiments, a composition is provided, comprising the compound of formula I, III, IV, V, or X and an EDTA irrigant, and a lubricant.

In other embodiments, a composition is provided, comprising the compound of formula I, III, IV, V, or X and a calcium hydroxide paste.

In other embodiments, a composition is provided, comprising the compound of formula I, III, IV, V, or X and zirconium oxide.

In other embodiments, a composition is provided, comprising the compound of formula I, III, IV, V, or X and an acrylic for dentures.

In other embodiments, a composition is provided, comprising the compound of formula I, III, IV, V, or X and a denture adhesive.

In other embodiments, a composition is provided, comprising the compound of formula I, III, IV, V, or X and a glaze for dentures.

In other embodiments, a dental sealant is provided, comprising the compound of formula I, III, IV, V, or X and a sealant.

In other embodiments, a dental material is provided, comprising the compound of formula I, III, IV, V, or X and calcium triphosphate.

In other embodiments, a filler material is provided, comprising the compound of formula I, III, IV, V, or X and a filler. In certain embodiments, the filler is at least one material selected from the group consisting of carbonate (such as calcium carbonates, sodium carbonate, sodium bicarbonate, magnesium carbonate, and dolomite), sulfate, silica, silicate aluminosilicate, phosphate, oxide, hydroxide, carbon, carbon fiber, iron-based filler, fiberglass, glass spheres, tricalcium aluminate, tetracalcium aluminoferrite, cement, modified cement, Portland cement, saccharide, fly ash, slag, and mixtures thereof. In certain embodiments, the filler material is a dental filler material. Suitable filler materials include tricalcium phosphate, zirconium oxide, calcium silicates, lithium disilicates, calcium phosphate monobasic, tetraalumoxide, barium sulfate, bismuth oxide, tricalcium silicate, dicalcium silicate, tricalcium aluminate, tetracalcium aluminoferrite, gypsum, calcium sulfate $2H_2O$, cement, modified cement, Portland cement, and mixtures thereof. In certain embodiments, the filler material, further comprises a material selected from the group consisting essentially of: sodium monofluoro-phosphate, stannous fluoride, zinc oxide, eugenol-2-methoxy-4(2-propenyl)phenol, mineral oil, and titanium dioxide, and mixtures thereof.

In other embodiments, a composite material is provided, comprising a filler and a compound of formula I, III, IV, V, or X.

In other embodiments, a dental prophylactic paste/silica is provided, comprising the compound of claim formula I, III, IV, V, or X.

In other embodiments, a composition is provided, comprising the compound of formula I, III, IV, V, or X and a fluoride varnish.

In other embodiments, a composition is provided, comprising the compound of formula I, III, IV, V, or X and a dental resin.

In other embodiments, a dental tray is provided, said dental tray treated with the compound of formula I, III, IV, V, or X. In certain embodiments, the dental tray is a fluoride tray. In certain embodiments, the dental tray is a whitening tray. In certain embodiments, the dental tray further comprises fluoride. In certain embodiments, a dental tray is provided, wherein the dental tray comprising a whitening tray treated with a compound of formula I, III, IV, V, or X.

In other embodiments, a method of oral irrigation of subgingivival tissues of the mouth is provided, said method comprising using a compound of formula I, III, IV, V, or X as an irrigant. In certain embodiments, the oral irrigation is an ultrasonic scaler using a compound of formula I, III, IV, V, or X.

In other embodiments, a method of desensitizing a tooth in an oral cavity is provided, the method comprising treating a tooth with a compound of formula I, III, IV, V, or X.

In other embodiments, a method of bonding filler material in a tooth is provided, the method comprising treating the tooth to receive the filler material, treating the treated tooth with a compound of formula I, III, IV, V, or X, placing the filler material in contact with the compound. In certain embodiments, the method of treating the tooth to receive the filler material is the use of acid etching.

In other embodiments, a method of bonding filler material in a tooth, the method comprising treating the tooth to receive a filler material, filling the treated tooth with a filler material that has been combined with a compound of formula I, III, IV, V, or X.

In other embodiments, a composition is provided comprising a composite material in combination with a compound of formula I, III, IV, V. or X.

In other embodiments, a method is provided for bonding a composite to a substrate, said method comprising treating the substrate to be bonded with a compound of formula I, III, IV, V, or X and applying the composite to the treated surface.

In other embodiments, an adhesive composition is provided comprising a compound of formula I, III, IV, V, or X. In certain embodiments, the method comprises treating a substrate with the adhesive composition described herein and applying the second substrate to the treated substrate. In certain embodiments, the method comprises adding the adhesive composition described herein to the non-solid material, and then placing the non-solid material on a substrate.

The materials are liquids as prepared. In some cases, if preferred, the by-produced alcohols and any residual water can be removed to provide a solid material, and in some cases the solid material is hard and appears to be almost crystalline and in some cases, the material is waxy or paste-like.

The curable, antimicrobial compositions of the invention may be used in a wide variety of applications where a curable polymer with antimicrobial properties is needed, especially applications requiring adhesion and flexural strength, including, but not limited to, dental applications: dental bonding agents, dental primers, dental filler materials, dental impression materials, dental casts and model material, composite filling materials, additives to existing dental bonding agents, tubule penetration fluids tooth desensitizers, sutures, fabrication of dentures, crowns, veneers, or other prostheses and orthodontics, and applications where reduced polymerization shrinkage is desired;

medical applications: adhesives, coatings, fiber treatment, sutures, wound care, bandages, endotrachael tubes, blood bags, intravenous bags, lines, tubes, catheters, implants (including artificial eyes), prosthetic devices, and contact lenses;

industrial and others applications: PVC water lines, water filtration, food wraps; cosmetic and beauty supplies (artificial nails and adhesives therefor), plasticizers for thermoplastics; solar adhesives, military applications (Kevlar), electronic applications (telephones, cellular devices, computers, and the like).

In electronic applications, for example, an epoxy version of the compound of formula IV can be used to form conductors or insulators, depending upon the desired electrical properties of the final materials. As used herein, "antimicrobial" means a substance that kills or inhibits the growth of microorganisms, such as bacteria, fungi, virii, or protozoans, and including those that are attached to surfaces as biofilms.

In actual use, certain materials of this invention have found to be desensitizers for teeth. Most dramatically, these materials have been found to provide adhesion between various substrates.

For example, in dentistry, these materials have been found useful for making composites, for bonding fillers and composites into cavities in teeth, for bonding crowns and other dental structures and are found especially useful as additives to commercial dental adhesives per se. In addition, evaluation of the use of these materials on teeth has shown that when certain of these materials are applied to teeth, the material is absorbed by the teeth, that is, teeth have microscopic tubules that run through the enamel to the dentin of the tooth. These tubules are capable of allowing transportation of microbes throughout the tooth. It is believed that if these tubules could be blocked, plugged, or filled, then one could prevent the passing and movement of microbes through teeth.

Such is the case with certain materials of this invention wherein, it has been found that the material passes into the tubules at least 20 times further than any existing adhesive or dental composition existing at this time. When in the tubules, the material cures and provides a plug in the tubules. Thus, the movement and passage of the microbes in the tooth can be avoided, leading to a healthier environment for teeth and the body in general.

Certain of these materials are good adhesives for filler material for dental use. In addition, it has been found that mixing the certain materials of this invention with common materials used in dental composites provides an improved composite having adhesive properties.

A most notable dental composition of this invention is the use of an acrylate bearing novel composition of this invention along with at least one acrylate monomer. The monomers can be independently selected from, acrylates, methacrylates, and a combination of acrylates and methacrylates. Suitable acrylates and methacrylates are monofunctional acrylates, difunctional acrylates, trifunctional acrylates and tetrafunctional acrylates or mixtures thereof. Also included with the scope of this invention are the use of photoinitiators for the acrylate monomers, such as, for example, aminoalkylphenone (such as Irgacure 369), bis acyl phosphine oxide (such Irgacure 819), bis 2,4,6 trimethylbenzoyl phenyl phospineoxide (such as Irgacure 819), oligo{2-hydroxy-2-methyl-1-{4-(i-methylvinyl)phenyl}propanone (such as Esacure KIP 150), which are all available from Sartomer, and a synergist, for example, ethyl-4-(N,N'-dimethylaminobenzoate. Such compositions for use in dental work are cured using blue light.

In other embodiment, the invention is directed to compositions, comprising:
   a compound of formula I, III, IV, V, or X;
   Portland cement; and
   optional radiopacifier.
In other embodiment, the invention is directed to compositions, comprising:
   a compound of formula I, III, IV, V, or X; and
   cement, comprising:
      about 50% by weight to about 70% by weight, based on the total weight of cement, of calcia;
      about 15% by weight to about 29% by weight, based on the total weight of cement, of silica;
      less than about 0.5% by weight, based on the total weight of cement, of iron oxide; and
      optional radiopacifier.
Suitable Portland cement, cement, and optional radiopacifiers are described in U.S. Pat. No. 7,892,342, which is incorporated herein by reference in its entirety.

In certain embodiments, at least a portion of the compound selected from the group of formula IV and formula V is sorbed (adsorbed or absorbed) on said filler. The use of a filler onto which the compound of formula IV or IV is sorbed permits any alcohol, such as methanol (in the embodiment where R is methyl), to be stripped off. This permits the product to be used in dental and medical application where methanol would otherwise render is unsuitable. Accordingly, the compositions are then particularly well-suited for toothpaste and mouthwash applications.

In certain embodiments, $R^a$ may additionally include a non-curring group selected from amine, H, and F.

In certain embodiments of the compounds of formula IV, at least one of A, B, Y, and Z is

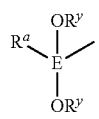

(covers 3-component).

Suitable fillers for use with compounds of formula I, III, IV, V, and X include, but are not limited to, carbonates (including calcium carbonate and dolomite), sulfates (such as barium sulfate and calcium sulfate), silicates (such as calcium silicate, tricalcium silicate, dicalcium silicate, zirconium silicate, aluminum silicate, feldspar, mica, nepheline syenite, talc, clay (i.e., kaolin), wollastonite, quartz, diatomite, lithium disilicates), phosphates (tricalcium phosphate, calcium phosphate monobasic), oxides (such as silicon dioxide, titanium dioxide, zirconium oxide, tetraalumoxide, bismuth oxide), hydroxides (such as aluminum trihydroxide and magnesium hydroxide), carbon (such as graphite and carbon black), iron-based fillers (such as cementite/carbon ($Fe_3C/C$), iron/cementite ($Fe/Fe_3C$) and iron/carbon (Fe/C), fiberglass, glass spheres, tricalcium aluminate, tetracalcium aluminoferrite, gypsum, calcium sulfate $2H_2O$, cement, modified cement, Portland cement, and mixtures thereof. Suitable fillers include nano-fillers.

In certain embodiments of the compositions comprising compounds of formula I, III, IV, V and X and filler, the silicate is at least one material selected from the group consisting of silica, aluminosilicate, calcium silicate, and combinations thereof. Suitable silicas include precipitated silica, fumed silica, colloidal silica, or a combination thereof.

Properties for some suitable silica and calcium silicates available from Huber are shown below:

| | Zeodent 103 | Zeodent 113 | Zeodent 165 | Zeodent 250 |
|---|---|---|---|---|
| Type | Silica | Silica | Silica | Ca Silicate |
| pH | 7.5 | 7.1 | 6.9 | 9.8 |
| Particle size | 8 um | 9 um | 14 um | 18 um |
| % water | 7.4 | 5.7 | 6.3 | 5.0 |

In certain embodiments, the compositions comprising compounds of formula IV or formula V and filler further comprise Portland cement.

In certain embodiments, the compositions comprising compounds of formula IV or formula V and filler further comprise cement, comprising:
   about 50% by weight to about 70% by weight, based on the total weight of cement, of calcia;
   about 15% by weight to about 29% by weight, based on the total weight of cement, of silica;
   less than about 0.5% by weight, based on the total weight of cement, of iron oxide; and
   optional radiopacifier.

In certain embodiments, the compositions comprising compounds of formula IV or formula V with or without filler further comprise at least one natural rubber, synthetic rubber, or a combination thereof.

In other embodiment, the invention is directed to compositions, comprising:
   at least one compound selected from the group of formula IV and formula V:

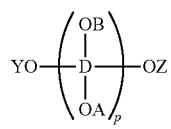

IV

-continued

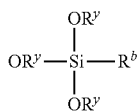
V (covers 2- and 3-component) (covers 1-component)
wherein:
p is 1 to about 5;
D is Si, Ti, Al, or Zr;
A, B, Y, and Z are each independently selected group consisting of H, $C_1$-$C_4$alkyl,

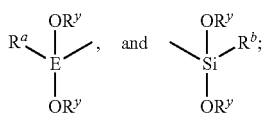

E is Si or Ti;
$R^a$ is a curing group selected from acrylate, methacrylate, vinyl, glycidyloxy, epoxy, ester, and isocyanate;
$R^b$ is independently —($C_3$-$C_6$)alkylenyl-dimethyl-($C_6$-$C_{22}$alkyl) quaternary ammonium chloride or —($C_3$-$C_6$) alkylenyl-methyl-phenyl-($C_6$-$C_{22}$alkyl) quaternary ammonium chloride;
each $R^y$ is, independently, H or $C_1$-$C_4$alkyl; and
wherein at least one of A, B, Y, and Z is

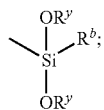

and
optionally, at least one filler;
wherein said compound of formula IV or formula V is sorbed onto said filler.

In certain embodiments, the compositions described herein further comprise at least one natural rubber, synthetic rubber, or a combination thereof. In certain other embodiments, the compositions further comprise at least one first polymer selected from the group consisting of thermoplastic polymer, thermosetting polymer, and mixtures thereof.

In certain embodiments, the compositions comprising compounds of formula IV or formula V with or without filler further comprise at least one first polymer selected from the group consisting of thermoplastic polymer, thermosetting polymer, and mixtures thereof.

Suitable thermoplastic polymers for use in the compositions of the invention include, but are not limited to, polyethylene, polypropylene, polyvinyl chloride, polyester, acrylic, methacrylic, or a copolymer or mixture thereof.

Suitable thermosetting polymers for use in the compositions of the invention include, but are not limited to, epoxy, polyester, alkyd, diallyl phthalate, melamine, polybutadiene, phenolic, silicone, urea, urethane, imide, or a mixture thereof.

In certain embodiments, the compositions of the invention are in the form of a powder. In certain embodiments, the compositions of the invention are in the form of a master batch. A "master batch," as used herein, is a product in which additives are dispersed (usually well dispersed) in a carrier material that is compatible with the main polymer or plastic in which it will be let down and may be supplied in a granule, a pellet, or a powder form. In certain embodiments, the compositions of the invention further comprise a second polymer that is the same or different from the first polymer.

In certain embodiments, the compositions comprising compounds of formula IV or formula V with or without filler further comprise at least one first polymer wherein said first polymer is:
 acrylonitrile-butadiene-styrene;
 acetal;
 acrylic;
 methacrylic;
 cellulosic (such as acetate, butyrate, ethyl cellulose, nitrate, propionate);
 ethylene copolymers (such as ethylene methyl acrylate, ethylene-n-butyl acrylate, ethylene vinyl acetate, ethylene methyl acrylic acid, ethylene acrylic acid, ethylene ethyl acrylate);
 fluoropolymer (such as fluorinated ethylene propylene, polytetrafluoroethylene, chlorotrifluoroethylene, polyvinylidene fluoride, ethylene tetrafluoroethylene-ethylene chlorotrifluoroethylene);
 nylon (such as nylon 6/6, 6, 6/10, 8, 12, and copolymers thereof);
 polyarylate;
 polyarylsufone;
 polybutylene;
 polycarbonate;
 polycarbonate-acrylonitrile-butadiene-styrene alloy;
 polyesters (such as polyethylene terephthalate, polybutylene terephthalate, polytetramethylene terephthalate, and copolymers thereof);
 polyetheretherketone;
 polyetherimide;
 polyethersulfone;
 polyethylene (low density, linear low density, high density, high molecular weight);
 ionomer;
 polymethylpentene;
 polyphenylene oxide;
 polyphenylene sulfide;
 polyimide;
 polypropylene (general purpose, impact copolymers, random copolymers);
 polystyrene (general purpose, high impact, medium impact);
 polysulfone;
 polyurethane;
 polyvinyl chloride;
 chlorinated polyvinyl chloride;
 polyvinyl chloride-acrylic;
 polyvinyl chloride-acrylonitrile-butadiene-styrene;
 styrene acrylonitrile;
 styrene maleic anhydride;
 thermoplastic elastomer;
 thermoplastic vulcanizate; or
 a copolymer or a mixture thereof.

In certain embodiments, the compositions comprising compounds of formula I, III, IV, V, or X and filler further comprise at least one thermoplastic polymer, thermosetting polymer, or a combination thereof. Suitable thermoplastic polymers include, but are not limited to, polyethylene, polypropylene, polyvinyl chloride, polyesters, and the like, copolymers and mixtures thereof.

In certain embodiments, the compositions comprising compounds of formula I, III, IV, V, or X with or without filler are useful as polymeric articles, such as film, sheet, container, foam container, bottle, crate, plastic parts, toys, pipe, foam insulation, panel, plastic lumber, or the like. In certain embodiments, the polymeric article is prepared by blown film, cast film, extrusion (such as profile extrusion, sheet extrusion, and foam extrusion), roto-molding, injection molding, blow molding, foamed, coating, or a combination thereof or the like.

In certain embodiments, the compositions comprising compounds of formula I, III, IV, V, or X with or without filler are useful as toothpaste, mouthwash, contact lenses (for example in heat curable systems with HEMA and a small amount of ethyleneglycol methacrylate), artificial nails and adhesives therefor, and the like.

In other embodiment, the invention is directed to methods of preparing a polymer, comprising:
providing at least one composition comprising the compound of formula IV, described herein;
hydrolyzing said compound of formula IV to form a hydrolyzed compound of formula IV; and
reacting said hydrolyzed compound of formula IV with at least one co-monomer. In certain preferred embodiments, the invention is directed to methods of preparing a polymer, comprising:
providing at least one composition comprising the compound of formula IV, described herein;
substantially fully hydrolyzing said compound of formula IV to form a substantially fully hydrolyzed compound of formula IV; and
reacting said substantially fully hydrolyzed compound of formula IV with at least one co-monomer.
In certain embodiments, the co-monomer is selected from the group consisting of ethylene, propylene, vinyl chloride, acrylate, methacrylate, and combinations thereof, preferably, the co-monomer is methyl methacrylate. The method may be carried with or without the addition of external heat. In certain preferred embodiments, the method is carried out without the addition of external heat. In certain embodiments, the method further comprises removing water and organic solvent, if present.

The compounds of formula IV or formula X may be used to increase the contact angle (and hence increase the surface energy) of compositions into which they are incorporated. Thus, the compounds of the invention are useful in methods of increasing the printability and/or dyeability of a polymeric composition. For example, this would lead to better print quality and permitting use of environmentally-friendly water-based inks in the place of solvent-based inks. Such methods comprise incorporating the compound of formula IV or formula X into a polymeric composition, either as a separate component or as a residue in the polymer itself (by polymerizing with at least one co-monomer).

The compounds of formula IV or formula X may be used to increase the hydrophilicity, improve antistatic properties, and reduce surface resistivity (by attracting water) of the compositions into which they are incorporated. Such methods comprise incorporating the compound of formula IV or formula X into a polymeric composition, either as a separate component or as a residue in the polymer itself (by polymerizing with at least one co-monomer).

The present invention is further defined in the following Examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1: Preparation of Methacrylate Curable, Antimicrobial Silicon-Containing Compounds The curable, antimicrobial silicon-containing compounds of the invention were prepared by mixing with constant agitation in the proper molar ratio of the three reactants:
Reactant 1: Compound having silane functionality
Reactant 2: Compound having silane functionality and methacrylate curable moiety
Reactant 3: Compound having silane functionality and antimicrobial moiety to form the reaction product of the invention.

If desired, water was then added to the reaction product of formula I to hydrolyze at least a portion of the hydrolyzable groups present on the molecule.

Several curable, antimicrobial compounds were prepared according to this method. The results are shown in Table 1:

TABLE 1

| Sample | Reactant 1 Tetraethoxy silane (TEOS) | Reactant 2 Methacryloxypropyl trimethoxysilane (Z-6030) | Reactant 3 Octadecyldimethyl Trimethoxysilylpropyl Ammonium chloride (at 42%) (Siquat 5700) | Water (pH 10) (except where noted) | Observations |
|---|---|---|---|---|---|
| 1 | 13.45 g | 7.64 g | 7.64 g | 8.62 g | Gel/2 phase |
| 2 | 13.45 g | 7.64 g | 7.64 g (3.2 g) | | |
| 3 | 2.08 g (1 mole) | 4.96 g (2 moles) | 23.6 g (9.92 g) (2 moles) | 1.8 g (10 m) | Clear/1 phase |
| 4 | 2.08 g (1 mole) | 4.96 g (2 moles) | 23.6 g (9.92 g) (2 moles) | 1.8 g (10 m) 1.8 g (20 m) 1.8 g (30 m) 1.8 g (40 m) | Clear/1 phase Clear/1 phase Clear/1 phase 2 phase |
| 5 | 2.08 g (1 mole) | 4.96 g (2 moles) | 23.6 g (9.92 g) (2 moles) | 1.8 g (10 m) 1.8 g (20 m) | |
| 6 | 2.08 g (1 mole) | 7.44 g (3 moles) | 11.8 g (4.98 g) (1 mole) | 1.8 g (10 m) 1.8 g (20 m) | Clear Clear |
| 7 | 2.08 g (1 mole) | 2.48 g (1 mole) | 35.4 g (17.9 g) (3 moles) | 1.8 g (10 m) 1.8 g (20 m) | Clear Clear |

TABLE 1-continued

| Sample | Reactant 1 Tetraethoxy silane (TEOS) | Reactant 2 Methacryloxypropyl trimethoxysilane (Z-6030) | Reactant 3 Octadecyldimethyl Trimethoxysilylpropyl Ammonium chloride (at 42%) (Siquat 5700) | Water (pH 10) (except where noted) | Observations |
|---|---|---|---|---|---|
| 8 | 2.08 g (1 mole) | 8.68 g (3.5M) | 5.9 g (2.48 g) (0.5M) | 1.8 g (10 m) 1.8 g (20 m) | Clear Cloudy |
| 9 | 2.08 g (1 mole) | 7.44 g (3 moles) | 11.8 g (4.98 g) (1 mole) | 1.8 g (10 m) 1.8 g (20 m) | Clear Clear |
| 10 | 2.08 g (1 mole) | 7.44 g (3 moles) | 11.8 g (4.98 g) (1 mole) | 1.8 g (10 m) 1.8 g (20 m) 1.8 g (30 m) 0.7 g 1.48 g 0.6 g | Clear Clear Clear Clear Clear Cloudy |
| 13 | 2.08 g (1 mole) | 7.44 g (3 moles) | 11.8 g (4.98 g) (1 mole) | 1.8 g (10 m) 1.8 g (20 m) | Clear Clear |
| 14 | 2.08 g (1 mole) | 7.44 g (3 moles) | 11.8 g (4.98 g) (1 mole) | 1.8 g (10 m) 1.8 g (20 m) 1.8 g (30 m) 0.7 g 1.48 g 0.6 g | Clear Clear Clear Clear Clear Cloudy |
| 32 | 2.08 g (1 mole) | 9.92 g (4 moles) | | 1.08 g (pH 2) 0.8 g (pH 2) | |
| 33 | 2.08 g (1 mole) | | 47.2 g (18.2 g) (4 moles) | 1.8 g (pH 2) | |
| 34 | 13.45 g | 7.64 g | 7.64 (3.2 g) | | |
| 38 | 4.16 g (1 mole) | 14.88 g (3 moles) | 23.6 g (9.96 g) (3 moles) | 3.6 g (pH 2) 3.6 g (pH 2) | Clear Clear |
| 39 | 2.08 g (1 mole) | 2.48 g (1 mole) | 35.4 g (17.9 g) (3 moles) | 1.8 g (pH 2) 1.8 g (pH 2) | Clear Clear |

Example 2: Curing of Methacrylate Curable, Antimicrobial Silicon-Containing Compounds The curable, antimicrobial silicon-containing compounds of the invention were prepared by mixing with constant agitation in the proper molar ratio of the three reactants:

Reactant 1: Compound having silane functionality
Reactant 2: Compound having silane functionality and methacrylate curable moiety
Reactant 3: Compound having silane functionality and antimicrobial moiety to form the reaction product of the invention.

Water was then added to the reaction product of formula I to hydrolyze at least a portion of the hydrolyzable groups present on the molecule.

A photoinitiator and a synergist were then added to the hydrolyzed product. HEMA, bisGMA, TEGDMA, and/or HDDMA was/were also added.

Several curable, antimicrobial compounds were cured according to this method. The results are shown in Table 2:

TABLE 2

| Sample | Reactant 1 Tetra-ethoxy silane (TEOS) | Reactant 2 Methacryloxy propyl-trimethoxy silane (Z-6030) | Reactant 3 Octa-decyldimethyl Trimethoxysilyl propyl Ammonium chloride (at 42%) (Siquat 5700) | Water (pH 2) | Photo-initiator (camphor quinone) | Synergist | HEMA | Bis-GMA | TEGDMA | HDDMA | Observations |
|---|---|---|---|---|---|---|---|---|---|---|---|
| 11 | 2.08 g (1 mole) | 7.44 g (3 moles) | 11.8 g (4.98 g) (1 mole) | 1.8 g (10 m) 1.8 g (20 m) | 0.149 g | 0.149 g | | | | | Clear Clear Bright yellow |
| 12 | 2.08 g (1 mole) | 2.48 g (1 mole) | 35.4 g (17.9 g) (3 moles) | 1.8 g (10 m) 1.8 g (20 m) | 0.226 g | 0.226 g | | | | | Clear Clear Bright yellow |
| 15 | 2.08 g (1 mole) | 7.44 g (3 moles) | 11.8 g (4.98 g) (1 mole) | 1.8 g (10 m) 1.8 g (20 m) | 0.26 g | 0.2 g | 85.5 g | | | | Clear Clear Bright yellow |

TABLE 2-continued

| Sample | Reactant 1 Tetraethoxy silane (TEOS) | Reactant 2 Methacryloxy propyltrimethoxy silane (Z-6030) | Reactant 3 Octadecyldimethyl Trimethoxysilyl propyl Ammonium chloride (at 42%) (Siquat 5700) | Water (pH 2) | Photo-initiator (camphor quinone) | Synergist | HEMA | Bis-GMA | TEGDMA | HDDMA | Observations |
|---|---|---|---|---|---|---|---|---|---|---|---|
| 16 | 2.08 g (1 mole) | 2.48 g (1 mole) | 35.4 g (17.9 g) (3 moles) | 1.8 g (10 m) 1.8 g (20 m) | 0.2 g | 0.2 g | 77.54 g | | | | Clear Clear Bright yellow |
| 17 | 3.36 g | 1.91 g | 1.91 g (0.8 g) | 0.45 g (* M) 0.45 g (* M) | 0.2 g | 0.2 g | 7.18 g | 18.875 g | | | Clear Clear Bright yellow |
| 18 | 2.08 g (1 mole) | 7.44 g (3 moles) | 11.8 g (4.98 g) (1 mole) | 1.8 g (10 m) 1.8 g (20 m) | 0.09 g | 0.09 g | | 1.81 g | 1.81 g | | Clear Clear 24 h liquid |
| 19 | 2.08 g (1 mole) | 7.44 g (3 moles) | 11.8 g (4.98 g) (1 mole) | 1.8 g (10 m) 1.8 g (20 m) 1.8 g (30 m) 1.8 g (40 m) | 0.14 g | 0.14 g | | 1.81 g | 12.5 g 1.81 g | | pH 2.0 Clear Clear Clear Clear 24 h 2 phase |
| 20 | 2.08 g (1 mole) | 2.48 g (1 mole) | 35.4 g (17.9 g) (3 moles) | 1.8 g (10 m) 1.8 g (20 m) | 0.14 g | 0.14 g | | 2.81 g | | 2.81 g | Clear White Cloudy 24 h liquid |
| 21 | 2.08 g (1 mole) | 2.48 g (1 mole) | 35.4 g (17.9 g) (3 moles) | 1.8 g (10 m) 1.8 g (20 m) 1.8 g (30 m) 1.8 g (40 m) | 0.14 g | 0.14 g | | 2.81 g | | 2.81 g | pH 2.0 Clear Clear Cloudy Cloudy 24 h 2 phase |
| 22 | 2.08 g (1 mole) | 2.48 g (1 mole) | 35.4 g (17.9 g) (3 moles) | 1.8 g (10 m) 1.8 g (20 m) | 0.28 g | 0.28 g | | 2.81 g | | 2.81 g | Clear White |
| 23 | 2.08 g (1 mole) | 7.44 g (3 moles) | 11.8 g (4.98 g) (1 mole) | 1.8 g (10 m) 1.8 g (20 m) | 0.18 | 0.18 | | | 1.81 g | 1.81 g | pH 2.0 Clear Clear |
| 24 | 2.08 g (1 mole) | 7.44 g (3 moles) | 11.8 g (4.98 g) (1 mole) | 1.8 g (10 m) 1.8 g (20 m) | 0.18 g | 0.18 g | | | 1.81 g | 1.81 g | pH 2.0 |

TABLE 2-continued

| Sample | Reactant 1 Tetraethoxy silane (TEOS) | Reactant 2 Methacryloxy propyl-trimethoxy silane (Z-6030) | Reactant 3 Octadecyldimethyl Trimethoxysilyl propyl Ammonium chloride (at 42%) (Siquat 5700) | Water (pH 2) | Photo-initiator (camphor quinone) | Synergist | HEMA | Bis-GMA | TEGDMA | HDDMA | Observations |
|---|---|---|---|---|---|---|---|---|---|---|---|
| 25 | 2.08 g (1 mole) | 2.48 g (1 mole) | 35.4 g (17.9 g) (3 moles) | 1.8 g (10 m) 1.8 g (20 m) | 0.28 g | 0.28 g | 2.81 g | | | 2.81 g | |
| 35 | 2.08 g (1 mole) | 7.44 g (3 moles) | 11.8 g (4.98 g) (1 mole) | 1.8 g (10 m) 1.8 g (20 m) | 0.2 g | 0.2 g | | 85.5 g | | | Clear Clear Bright yellow Gel/bottom (5 days) |
| 36 | 3.36 g | 1.91 g | 1.91 g | 0.45 g 0.45 g | 0.07 g | 0.07 | | 7.18 g 18.75 g | | | Clear Clear Bright yellow |
| 37 | 2.08 g (1 mole) | 2.48 g (1 mole) | 35.4 g (17.9 g) (3 moles) | 1.8 g 1.8 g | 0.2 g | 0.2 g | | | | | Clear Clear Gel (5 days) |
| 49 | 2.5 g (1 mole) | 8.93 g (3 moles) | 14.6 g (6.13 g) (1 mole) | 2.16 | 0.21 g | 0.21 g | | | | | |
| 50 | 2.5 g (1 mole) | 8.93 g (3 moles) | 14.6 g (6.13 g) (1 mole) | 2.16 | 0.21 g | 0.21 g | | | | 4.34 | |

Example 3: Testing of Antimicrobial Activity

The curable, antimicrobial silicon-containing compounds of the invention were prepared by mixing with constant agitation in the proper molar ratio of the three reactants:
Reactant 1: Compound having silane functionality
Reactant 2: Compound having silane functionality and methacrylate curable moiety
Reactant 3: Compound having silane functionality and antimicrobial moiety to form the reaction product of the invention.

Optionally, water was then added to the reaction product of formula I to hydrolyze at least a portion of the hydrolyzable groups present on the molecule.

Several curable, antimicrobial compounds were prepared according to this method. Colony counts were taken on select samples in accordance with Standard Methods for examination and water and waste water (Test 9215A; Heterotrophic Plate Count) ($21^{st}$ edition). The results are shown in Table 3:

TABLE 3

| Sample | Reactant 1 Tetraethoxy silane (TEOS) | Reactant 2 Methacryloxy-propyl trimethoxy-silane (Z-6030) | Reactant 3 Octadecyldimethyl Trimethoxysilyl-propyl Ammonium chloride (at 42%) (Siquat 5700) | Water pH 2 | Water pH 7 | Water pH 10 | Final pH | Colony count |
|---|---|---|---|---|---|---|---|---|
| 26 | 8.32 g (1 mole) | 29.2 g (3 moles) | 47.2 g (1 mole) | 3.6 g | | | 2.0 | 0 |
| 27 | 8.32 g (1 mole) | 29.2 g (3 moles) | 47.2 g (1 mole) | | 3.6 g | | 6.0 | |
| 28 | 8.32 g (1 mole) | 29.2 g (3 moles) | 47.2 g (1 mole) | | | 3.6 g | 6.0-7.0 | |
| 29 | 4.16 g | 4.96 g | 70.8 g | 3.6 g | | | 3.0 | 0 |

TABLE 3-continued

| Sample | Reactant 1 Tetraethoxy silane (TEOS) | Reactant 2 Methacryloxypropyl trimethoxysilane (Z-6030) | Reactant 3 Octadecyldimethyl Trimethoxysilylpropyl Ammonium chloride (at 42%) (Siquat 5700) | Water pH 2 | Water pH 7 | Water pH 10 | Final pH | Colony count |
|---|---|---|---|---|---|---|---|---|
| 30 | 4.16 g | 4.96 g | 70.8 g | | 3.6 g | | 6.0 | |
| 31 | 4.16 g | 4.96 g | 70.8 g | | | 3.6 g | 7.0 | |

Example 4: Preparation of Vinyl Curable, Antimicrobial Silicon-Containing Compounds The curable, antimicrobial silicon-containing compounds of the invention were prepared by mixing with constant agitation in the proper molar ratio the three reactants:
Reactant 1: Compound having silane functionality
Reactant 2: Compound having silane functionality and vinyl curable moiety
Reactant 3: Compound having silane functionality and antimicrobial moiety to form the reaction product of the invention.

Water was then added to the reaction product of formula I to hydrolyze at least a portion of the hydrolyzable groups present on the molecule.

Several curable, antimicrobial compounds were prepared according to this method. The results are shown in Table 4:

TABLE 4

| Sample | Reactant 1 Tetraethoxy silane (TEOS) | Reactant 2 Vinyl triethoxysilane (VEO) | Reactant 2 n-Octyltrimethoxy silane (Z-6341) | Reactant 3 Octadecyldimethyl Trimethoxysilylpropyl Ammonium chloride (at 42%) (Siquat 5700) | Water (pH 10) |
|---|---|---|---|---|---|
| 40 | 2.08 g (1 mole) | 4.44 g (3 moles) | | 4.96 g (11.8 g) (1 mole) | 1.8 g 0.9 g |
| 41 | 2.08 g (1 mole) | 2.96 g (2 moles) | | 23.6 g (9.92 g) (2 mole) | 1.9 g 1.8 g |
| 42 | 2.08 g (1 mole) | 1.48 g (1 mole) | | 35.4 g (17.9 g) (2 mole) | 1.8 g 1.8 g |
| K-33 | 4.16 g | 4.72 g | | 70.85 g | 3.6 g |
| K-34 | 4.16 g | | 4.68 g | 70.09 g | 3.6 g |

Example 5: Preparation of Methacrylate Curable, Antimicrobial Compounds

The curable, antimicrobial silicon-containing compounds of the invention were prepared by mixing with constant agitation in the proper molar ratio of the three reactants:
Reactant 1: Compound having silicate, titanate, or zirconate or functionality (or a mixture thereof)
Reactant 2: Compound having silane or titanate functionality and methacrylate curable moiety
Reactant 3: Compound having silane functionality and antimicrobial moiety to form the reaction product of the invention.

Water was then added to the reaction product of formula I to hydrolyze at least a portion of the hydrolyzable groups present on the molecule.

Several curable, antimicrobial compounds were prepared according to this method. The results are shown in Table 5A:

TABLE 5A

| Sample | Reactant 1 Tetraethoxy silane (TEOS) | Reactant 1 Titanium n-butoxide (TBT) | Reactant 1 Zirconium n-propoxide (TPZr) (at 70%) | Reactant 2 Methacryloxypropyl trimethoxysilane (Z-6030) | Reactant 2 Titanium trimethacrylate methoxyethoxyethoxide (TiMAE) (at 70%) | Reactant 3 Octadecyldimethyl Trimethoxysilylpropyl Ammonium chloride (at 42%) (Siquat 5700) | Water (pH 10 except where noted) | Observations |
|---|---|---|---|---|---|---|---|---|
| 43 | | 3.4 g (1 mole) | | 7.44 g (3 moles) | | 11.8 g (4.96 g) (1 mole) | 1.8 g | Clear solution; slight yellow |

TABLE 5A-continued

| Sample | Reactant 1 Tetraethoxy silane (TEOS) | Reactant 1 Titanium n-butoxide (TBT) | Reactant 1 Zirconium n-propoxide (TPZr) (at 70%) | Reactant 2 Methacryloxypropyl trimethoxysilane (Z-6030) | Reactant 2 Titanium trimethacrylate methoxyethoxyethoxide (TiMAE) (at 70%) | Reactant 3 Octadecyldimethyl Trimethoxysilyl-propyl Ammonium chloride (at 42%) (Siquat 5700) | Water (pH 10 except where noted) | Observations |
|---|---|---|---|---|---|---|---|---|
| 44 | | | 3.27 g (1 mole) | 7.44 g (3 moles) | | 11.8 g (4.96 g) (1 mole) | 1.8 g | White; precipitate; 3 phase |
| 45 | | | | | 4.22 g (1 mole) | 11.8 g (4.96 g) (1 mole) | 1.8 g | 2 phase |
| 46 | | 3.4 g (1 mole) | | 7.44 g (3 moles) | | 11.8 g (4.96 g) (1 mole) | 1.8 g (pH 2) | Flocculation |
| 47 | | | 3.27 g (1 mole) | 7.44 g (3 moles) | | 11.8 g (4.96 g) (1 mole) | 1.8 g | White precipitate White precipitate |
| 48 | | | | | 4.22 g (1 mole) | 11.8 g (4.96 g) (1 mole) | 1.8 g | Hazy yellow Gel/Dissolve |
| T-1 | 3.4 g | | | 2.48 g | | 35.4 g (14.9 g) | 0.36 g 0.72 g | Milky white Milky white Clear, slight yellow |
| T-2 | 3.4 g | | | 4.96 g | | 23.6 g (9.91 g) | 0.36 g | Milky white Clear, slight yellow |
| T-3 | 3.4 g | | | 7.44 g | | 11.8 g (4.96 g) | 0.36 g | Milky white Clear, slight yellow |

Example 6: Curing of Curable, Antimicrobial Silicon-Containing Compounds in Dental Resin Testing indicated that addition of Sample 26 (see below) to a resin comonomer blend containing 70 weight % bisGMA and 30 weight % HEMA increased the degree of conversion of the relatively hydrophilic resin blend. The results are shown in FIG. 1.

Figure 2:
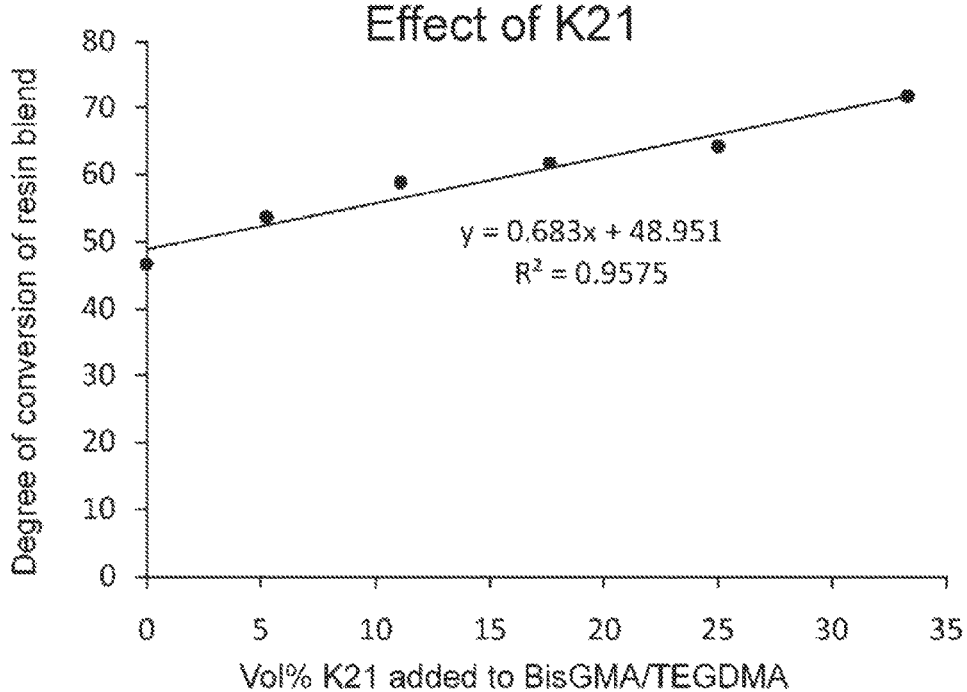
FIG. 2 is a plot of the effect of addition of different concentrations of Sample 33 on the degree of conversion of a hydrophilic resin blend consisting of BisGMA-TEGDMA.

Likewise, addition of Sample 33 (see below), a non-curable quaternary ammonium-functionalized silane to a resin comonomers blend consisting of 70 weight % Bis-GMA and 30 weight % TEGDMA increases the degree of conversion of the relatively hydrophobic resin blend. The results are shown in FIG. 2.

These results suggest, serendipitously, that the additional of quaternary ammonium-functionalized silanes to dental resins has the potential to improve the quality of resin composites and dentin adhesives currently available to clinicians by having materials that kill bacteria on contact as well as improved curing characteristics. However, as the quaternary ammonium silanes were added to existing resin comonomers blends with constant 70/30 compositions, it is possible that these results represent increases in the diluent effect of BisGMA which in turn, results in increasing the molecular mobility of the BisGMA molecule. BisGMA is highly viscous due to its molecular stiffness and intermolecular hydrogen bonding and has to be diluted with glycol dimethacrylates such as TEGDMA to facilitate handling. The potential disadvantages with the use of a TEGDMA diluent include its leaching potential and higher water sorption. Thus, a further study was conducted to examine whether the quaternary ammonium silanes may be used for substituting TEDGMA in resin composite formulations.

Experimental Design and Methods
1. Materials for Testing

Four quaternary ammonium silanes with methacrylate functional groups (Sample 26, Sample K18.5, Sample 27, and Sample 43) will be tested. These silanes (QASM) will be added in varying amounts to a generic BisGMA/TEGDMA resin comonomer blend so that the amount of diluent remains constant at 30 weight %:

| Comonomer Blends | Composition | Weight % |
|---|---|---|
| Blend 1 (CONTROL) | BisGMA | 68.75 |
| | TEGDMA | 30.00 |
| | QASM | 0.00 |
| | CQ | 0.25 |
| | DMAEMA | 1.00 |
| Blend 2 (Sample 26) | BisGMA | 68.75 |
| | TEGDMA | 20.00 |
| | QASM | 10.00 |
| | CQ | 0.25 |
| | DMAEMA | 1.00 |
| Blend 3 (Sample K18.5) | BisGMA | 68.75 |
| | TEGDMA | 10.00 |
| | QASM | 20.00 |
| | CQ | 0.25 |
| | DMAEMA | 1.00 |
| Blend 4 (Sample 27) | BisGMA | 68.75 |
| | TEGDMA | 5.00 |
| | QASM | 25.00 |
| | CQ | 0.25 |
| | DMAEMA | 1.00 |
| Blend 5 (Sample 43) | BisGMA | 68.75 |
| | TEGDMA | 0.00 |
| | QASM | 30.00 |
| | CQ | 0.25 |
| | DMAEMA | 1.00 |

2. Degree of Conversion

Each resin blend will be added to a Teflon mold that is covered by Mylar above and below the mold, and light-cured for 60 sec each on each side of the mold to create resin disks that are 6 mm in diameter and 1 mm thick (N=3). These resin disks are devoid of air-inhibition layers. The curing characteristics of the quaternary ammonium silane or titanate-incorporated polymerized resin blends will be examined using attenuated total reflection-Fourier transform-infrared spectroscopy (ATR-FTIR), according to the method reported by Ruyter (1981). Percent monomer conversion will be determined by comparing changes in the ratios of aliphatic (1638 cm$^{-1}$)-to-aromatic (1608 cm$^{-1}$) C=C absorption peaks in the uncured and cured states.

3. Shrinkage-Strain and Shrinkage Strain Rate

Figure 3:
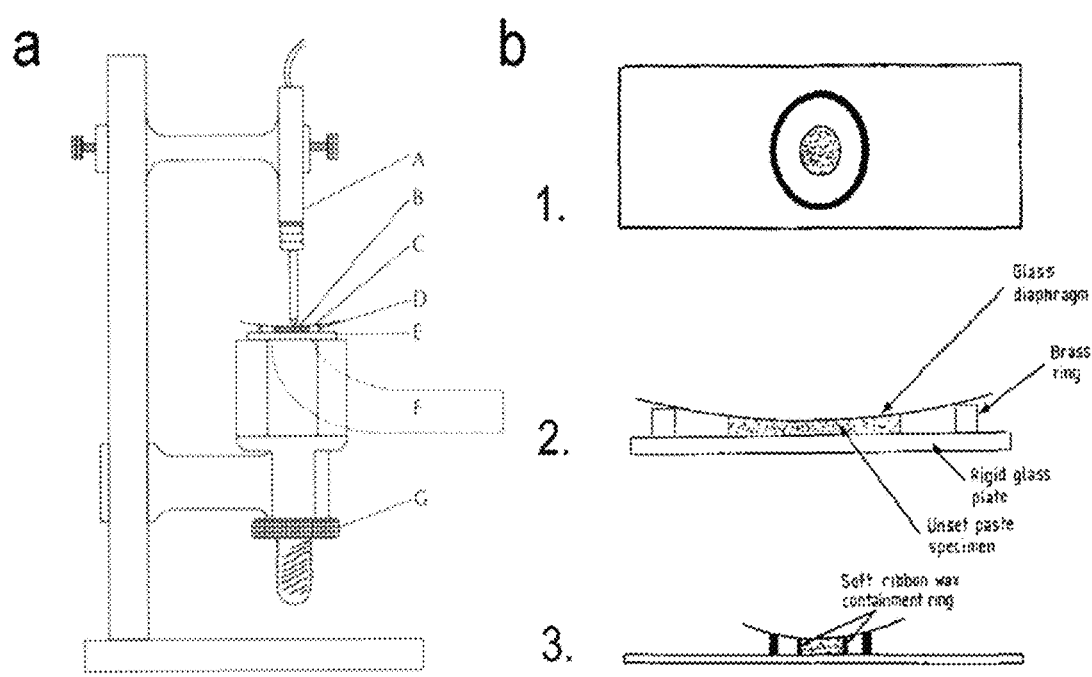
FIG. 3 is a schematic of the testing assembly showing the following: a. Schematic of the shrinkage test assembly: A, LVDT transducer, total length 90 mm; B, test specimen, diameter 8 mm; C, flexible diaphragm, thickness 0.13 mm; D, support ring, internal diameter 16 mm, height, 1.5 mm; E, rigid glass or quartz plate: F, fiber-optic light guide, exit diameter 8 mm; G, height adjustment screw. b. Resin specimen mounted on the rigid glass plate at the center of the brass support ring: (1) plan view; (2) elevation, with glass diaphragm in position; (3) wax containment ring used with low viscosity and unfilled resin specimens

The polymerization shrinkage-strain (%) of the different resin blends after incorporation of quaternary ammonium silane methacrylates will be measured using the bonded-disk method, as described by Watts and Cash (1991) (FIG. 3). Three replicates for each experimental resin will be made. Shrinkage-strain rates will be obtained by numerical differentiation of shrinkage-strain data, from which the maximum shrinkage-strain rate (%/sec) and the time at the maximum rate (sec) will be obtained.

4. Three-Point Flexure

Figure 4:
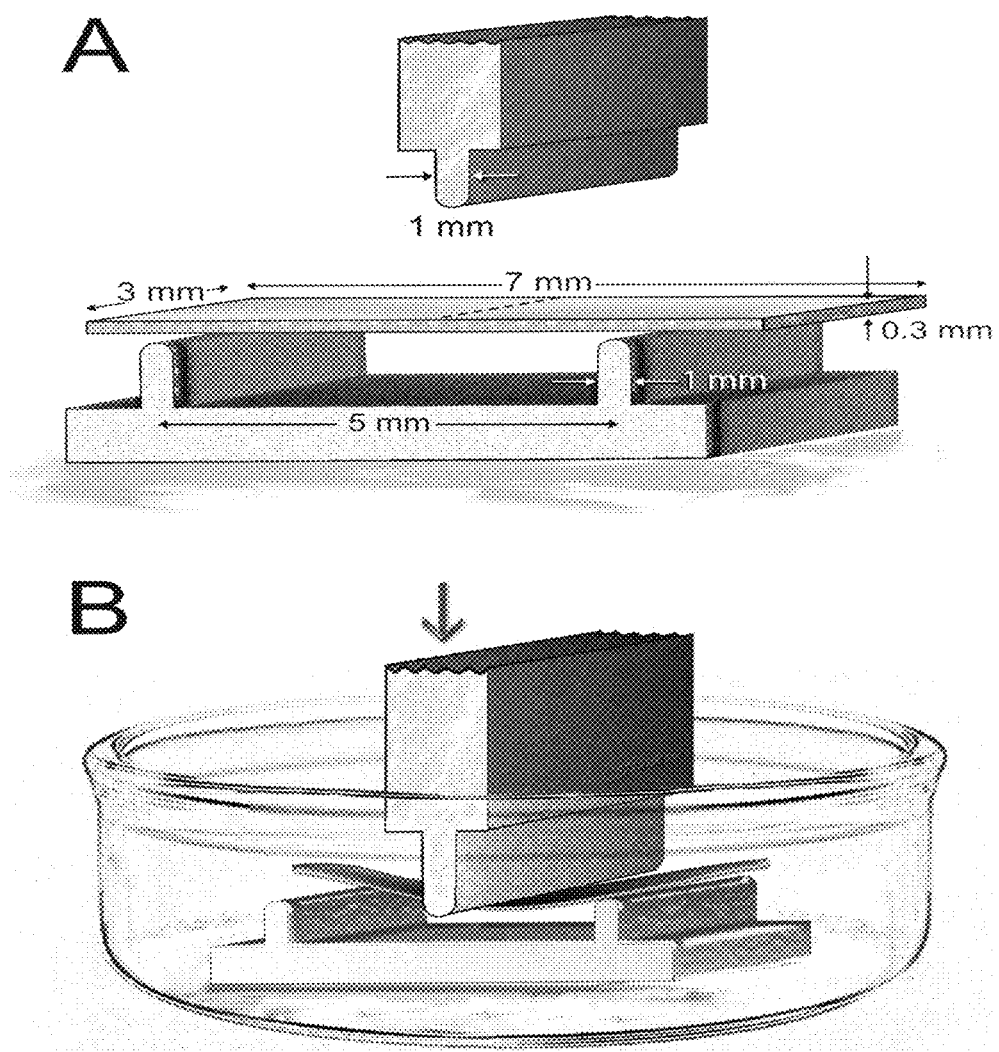
FIG. 4 shows two schematic drawings of the test equipment. A. A schematic showing the miniature three-point flexure device. Resin beams will be prepared to 0.30±0.01 mm thick to establish a span-to-depth ratio of approximately 16:1 in order to minimize shear and local deformation effects during three-point flexure. B. A schematic depicting three-point flexure of a resin beam to 2% strain in water.
Figure 5:
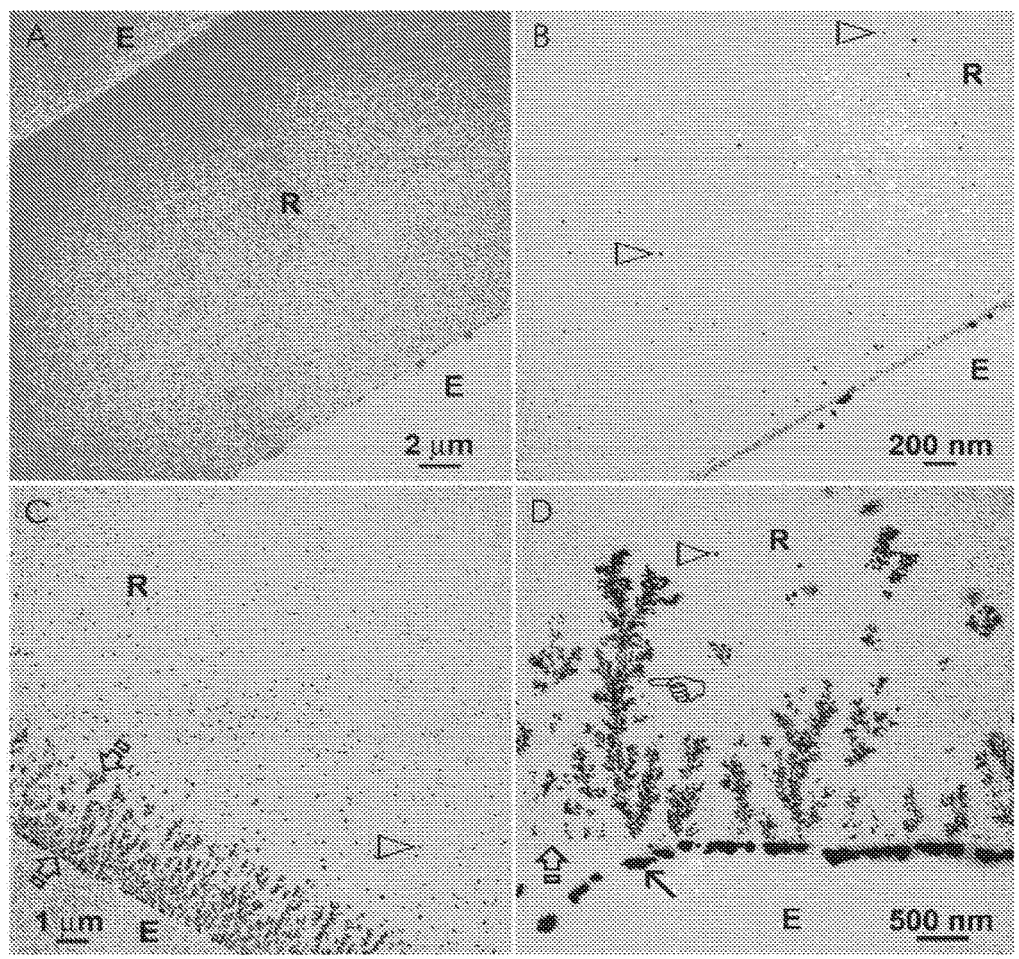
FIG. 5 shows transmission electron microscopy (TEM) showing the characteristics of the resin films. The resin film (R) was sandwiched between two layers of epoxy resin (E) for support during ultramicrotomy. The more silver grains there are in the resin film, the higher is its water permeability. A. A resin film with no silver deposition that is characteristic of Resin 1 (Bis-GMA-E+TEGDMA) and Resin 2 (Bis-GMA+TEGDMA). B. A high magnification view of Resin 3 (Bis-GMA+HEMA) in which only isolated silver grains (open arrowheads) were seen at high magnifications. These silver grains decreased in dimensions from the periphery to the center of the films. C. A resin film that is characteristic of Resin 4 (Bis-GMA+HEMA+TCDM) and Resin 5 (Bis-GMA+HEMA+2MP). Apart from the isolated silver grains (open arrowhead), a peripheral zone of branched water channels (water trees; between open arrows) could be identified along the periphery of the resin film. D. A high magnification of FIG. 5C, showing the emergence of the water channels (pointer) from the periphery of the resin film (open arrow). The surfaces silver deposits (arrow) were partially detached from the resin film. We want to compare the characteristics of the resin films after incorporation of different types of quaternary ammonium silanes.

Flexural testing will be performed using a miniature three-point flexure device (FIG. 4A), using 7×3×0.3 mm resin beams prepared from 10 mm diameter Teflon molds. Flexural properties of the resin beams (N=10) will be determined by centrally loading the polymer beams to fracture using a universal testing machine (Vitrodyne V100, Liveco Inc, Burlington, Vt.) at a crosshead speed of 1 mm/min. Stress-strain curves will be prepared from the load-displacement data, from which the flexural modulus, flexural strength and modulus of toughness (area under stress-strain curve) will be determined using a statistics/curve-fitting software. Additional resin beams will be stored in deionized water for 4 weeks and tested with three-point flexure by loading them to 2% strain in deionized water (FIG. 48) to obtain the respective flexural modulus before and after water storage.

5. Water Permeability of Resin Films

Resin films will be cast from each silane-incorporated resin blend by pipetting 60 μL of the respective resin blend onto a clean flat glass slab. The resin drop will then be covered with Mylar and a microscopic glass slide to enable the resin mixture to spread, forming a circular film with a diameter of approximately 5.5 cm. The resin film will then be light-cured from the top and bottom of the glass for 40 seconds each. The average thickness of each polymerized resin film can be calculated from the volume of resin solution used and the diameter of the resin film.

Each polymerized resin films will be immersed in a 50 weight % ammoniacal silver nitrate solution for 48 hours, according to the silver impregnation protocol reported by Tay et al. (2002). After immersion in the tracer solution, the silver-impregnated films will be rinsed thoroughly in distilled water and placed in a photodeveloping solution for 8 hours under a fluorescent light to reduce the diamine silver ion complexes to metallic silver. The silver impregnated films will then be processed for Transmission Electron Microscopy (TEM) by sandwiching each film between epoxy resins. Ninety nm thick sections, each containing the entire cross section of a piece of resin film, and polymerised epoxy resin from above and below will be prepared. They will be examined unstained using a transmission electron microscope operating at 110 kV (FIG. 4) to compare the water permeability characteristics of the five film versions before and after adding quaternary ammonium silanes.

6. Statistical Analysis

Two-factor ANOVAs and Tukey multiple comparison tests will be used to examine the effects of 1) the type of QASMs and 2) their concentrations on the degree of conversion, shrinkage strain, shrinkage strain rate and flexural strengths of the resin comonomers blend, seeking to identify the best QASM and the most optimal concentration for replacing TEGDMA in resin compositions. The data will first be examined to determine the validity of the normality (Shapiro-Wilk test) and equal variance assumptions (modified Levee test). If those assumptions appear to be violated, the data obtained will be analyzed using the ranked based version of the comparison statistics. Statistical significance will be set in advance at $\alpha=0.05$.

Examples 7 to 10: Sorption on Silica Filler

For Example 7: Huber 250 precipitated silica was dispersed in deionized water and then adjusted to pH 10 with sodium hydroxide. To this was added drop wise, Siquat 5772 antimicrobial (3-(trimethoxysilyl) propyldimethyloctadecyl ammonium chloride 72% non-volatile in methanol) and vinyltrimethoxysilane (VTM) under constant agitation. This was allowed to mix for 60 minutes. The solution was weighted; poured into a shallow glass dish, place in an air circulating oven at 45° C. for 24 hours. The dried powder was removed from the oven, reweighed, and ground using a motor and pistil.

For Example 8:

Part A: Siquat 5772 antimicrobial and VTM were placed in a beaker with agitation. Water at pH 10 was added drop wise allowing mixing for 60 minutes.

Part B: Zeodent 250 precipitated silica was dispersed in deionized water adjusted to pH 10 with sodium hydroxide.

Part A was slowly added to Part B under constant agitation. This was allowed to mix for 60 minutes. The solution was weighed; poured into a shallow glass dish, placed in an air circulating oven at 45° C. for 24 hours. The dried powder was removed from the oven, reweighed, and ground using a mortar and pestle.

Examples 9 and 10 were prepared using the same procedure as Example 8.

The formulation data for Examples 7 to 10 is shown in Table 6 with all amounts in grams.

TABLE 6

|  | 7 | 8A | 8B | 9A | 9B | 10A | 10B |
|---|---|---|---|---|---|---|---|
| Zeodent 103 silica |  |  |  |  |  |  | 25 |
| Zeodent 250 calcium silicate | 25 |  | 25 |  | 25 |  |  |
| Water pH 10 | 200 | 5 | 100 | 1.3 | 100 | 0.5 | 100 |
| Siquat 5772 antimicrobial @ 72% | 2.08 | 2.08 |  | 6.2 |  | 6.3 |  |

TABLE 6-continued

|  | 7 | 8A | 8B | 9A | 9B | 10A | 10B |
|---|---|---|---|---|---|---|---|
| VTM | 0.5 | 0.5 |  | 0.43 |  |  |  |
| Tetraethoxy silane (TEOS) |  |  |  | 0.5 |  | 0.5 |  |
|  |  | mix into 8B |  | mix into 9B |  | mix into 10B |  |
| Initial weight |  |  | 120.5 |  | 150.7 |  | 129.2 |
| Final weight |  |  | 28.25 |  | 32.44 |  | 32.49 |

The formulation used in Example 10 could be used as a toothpaste

Example 11: Sorption on Silica Filler

In another set of experiments, Siquat 5700 antimicrobial (3-(trimethoxysilyl) propyl dimethyl octadecyl ammonium chloride 42% in methanol) was diluted to 2% active in water at pH 10 and then added to the precipitated silicas (Zeodent 103, 113, 165 from Huber) and calcium silicate (Zeodent 250 from Huber) in the concentrations shown in the table below (amounts shown in grams). Mixing was done by hand until the water/5700 solution was well mixed into the silica. The formulation data is shown in Table 7.

TABLE 7

|  | p-1 | p-2 | p-3 | p-4 |
|---|---|---|---|---|
| Zeodent 103 silica | 20 |  |  |  |
| Zeodent 113 silica |  | 20 |  |  |
| Zeodent 165 silica |  |  | 10 |  |
| Zeodent 250 Ca silicate |  |  |  | 20 |
| Siquat 5700 (2% in pH 10 water) | 20 | 20 | 10 | 20 |
| Water | Thick paste | Clumpy powder 10.9 Thick paste | Fine powder 28.9 Thick paste | Fine powder 35 Thick paste |

Example 12: Polymer Carrier

Samples of the compounds of formula IV in a polymer carrier (methacrylic from bisGMA and HEMA; epoxy) were prepared in accordance with the table below (amounts in grams). The following abbreviations are used in the table:
bisGMA is bisphenol A bis(2-hydroxy-3-methacryloxypropyl) ether
HEMA is 2-hydroxyethylmethacrylate
Epoxy 324 is D.E.R. 324 epoxy resin from Dow Chemical Co.
TEOS is tetraethoxysilane
Z-6030 is methacryloxypropyltrimethoxysilane
Z-6040 is glycidoxypropyltrimethoxysilane
5772 is 3-(Trimethoxysilyl) Propyldimethyloctadecyl Ammonium Chloride 72.1%

| Sample | 12A | 12B | 12C | 12D |
|---|---|---|---|---|
| Polymer Base |  |  |  |  |
| Bis-GMA | 15.23 |  |  |  |
| HEMA |  | 30.46 | 7.6 | 30.4 |
| Epoxy 324 |  |  |  |  |
| TEOS | 8.32 | 16.64 | 4.16 | 16.64 |
| Z-6030 | 29.2 | 28.4 | 14.6 | 58.4 |
| Z-6040 |  |  |  |  |
| 5772 @ 72% NVC | 27.5 | 55 | 13.75 | 55 |
| Water @ pH 2 (HCl) | 3.6 | 7.2 | 7.2 clear | 28.8 |
| Water @ pH 2 |  |  | 19.8 cloudy | 40 |
| Water @ pH 2 |  |  |  | 39.2 |
| Water @ pH 10 (KOH) |  |  |  |  |
| Water @ pH 10 |  |  |  |  |
| Initial Weight | 83.85 | 137.7 | 67.11 | 268.44 |
| Time (min)/ temperature (° C.) | 20/75 30/80 60/90 80/75 Final | 30/70 60/78 | 30/65 60/80 90/85 final | 30/64 |

| | | | | | | | | | | |
|---|---|---|---|---|---|---|---|---|---|---|
| Net Weight | 69.91 | 65.52 | 64.42 | 63.07 | 62.88 | 117.72 | 106.4 | 54.78 cloudy | 43.3 clear | 32.6 clear | 29.74 clear | 233.82 cloudy |
| % recovery, actual | 74.99 | | | | | 77.27 | | 44.32 | | | | 45.03 |

| Sample | | 12E | 12F | |
|---|---|---|---|---|
| Polymer Base | | | | |
| Bis-GMA | | | | |
| HEMA | | 6.2 | | |
| Epoxy 324 | | | 30.4 | |
| TEOS | | 2.08 | 16.64 | |
| Z-6030 | | 7.44 | | |
| Z-6040 | | | 58.4 | |
| 5772 @ 72% NVC | | 6.89 | 55 | |
| Water @ pH 2 (HCl) | clear | | | |
| Water @ pH 2 | clear | | | |
| Water @ pH 2 | cloudy | | | |
| Water @ pH 10 (KOH) | | 2.88 | 28.8 | clear |
| Water @ pH 10 | | | 79.2 | cloudy |
| Initial Weight | | 25.49 | 268.44 | |
| Time (min)/ temperature (° C.) | 45/70  60/76  75/78  90/80  145/85  final | 60/85 | 150/93 | final |
| Net Weight | 203.82 cloudy  185.65 cloudy  170.02 cloudy  144.92 sl. opaque  129.04 clear  120.88 clear | 17.68 | 167.15 clear | 143.6 clear |
| % recovery, actual | | 69.36 | 53.49 | |

Samples 12B and 12F were formed into a coating with the addition of solvent, catalyst, photoinitiator, and synergist, as indicated in the table below (amounts in grams). Both formulations (12G and 12H) formed excellent coatings.

| Components | Formulation 12G | Formulation 12H |
|---|---|---|
| Sample 12B (methacrylate polymer carrier) | — | 20 |
| Sample 12F (epoxy polymer carrier) | 20 | — |
| Ethanol (solvent) | 10 | — |
| 29 catalyst from Dow Chemical | 0.58 | — |
| Camphorquinone (photoinitiator) | — | 0.04 |
| Ethyl-4-(dimethylamino)benzoate (synergist) | — | 0.02 |
| Cure conditions | 45° C./15 minutes | UV |
| Coating properties | Excellent, hard coating | Excellent coating |

Example 13: Preparation of Methacrylate Curable, Antimicrobial Compounds

The curable, antimicrobial silicon-containing compounds of the invention were prepared by mixing with constant agitation in the proper molar ratio of the three reactants:

Reactant 1: Compound having silicate functionality: tetraethoxysilane (TEOS)

Reactant 2: Compound having silane functionality and methacrylate curable moiety: methacryloxypropyltrimethoxysilane (Z-6030)

Reactant 3: Compound having silane functionality and antimicrobial moiety: 3-(trimethoxysilyl)propyldimethyloctadecyl ammonium chloride 72.1%) (5772)

to form the reaction product (QAMS-3) of the invention.

Water was then added to the reaction product of formula IV to fully hydrolyze the hydrolyzable groups present on the molecule.

The formulation data is shown in Table 8.

TABLE 8

| Component | Mass (grams) | Molar Ratio |
|---|---|---|
| TEOS | 20.833 | 1 |
| 5772 (72.1%) | 49.63 | 1 |
| Z-6030 | 74.52 | 3 |
| Water | 28.8 | 16 |
| Total | — | 260.183 |

The QAMS-3 product was then polymerized at various weight percentages (1%, 5%, 10%, 15%, and 20%) in methyl methacrylate without adding heat as shown in Table 9.

TABLE 9

| QAMS-3 Level (weight %) | Mass (grams) | QAMS (grams) | MMA (grams) |
|---|---|---|---|
| 1% | 40 | 0.4 | 39.6 |
| 5% | 40 | 2 | 38 |
| 10% | 40 | 4 | 36 |
| 15% | 40 | 6 | 34 |

Figure 6A:
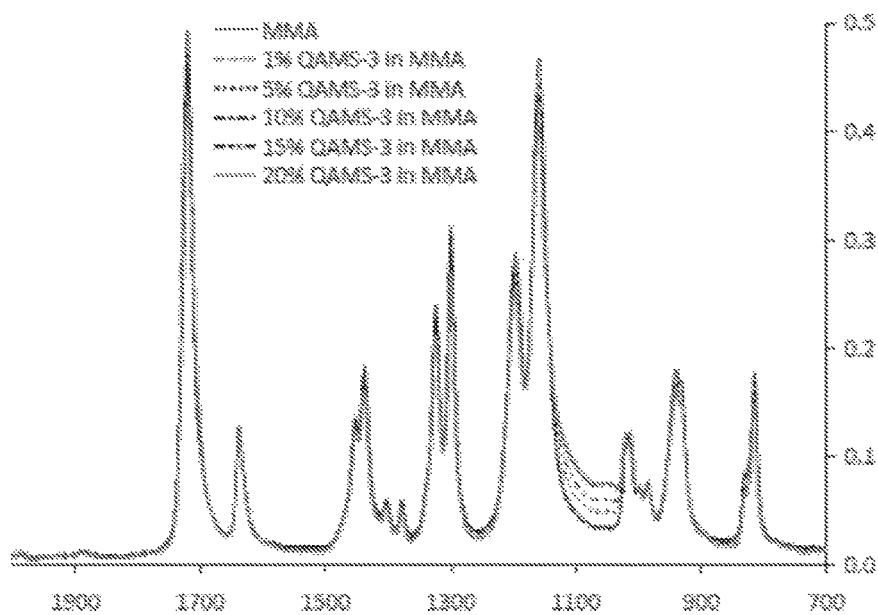
FIGS. 6A, 6B, and 6C show Fourier transform infrared spectroscopy (FTIR) spectra for the methacrylate polymer products containing QAMS at various weight levels (0, 1, 5, 10, and 20% by weight).
Figure 6B:
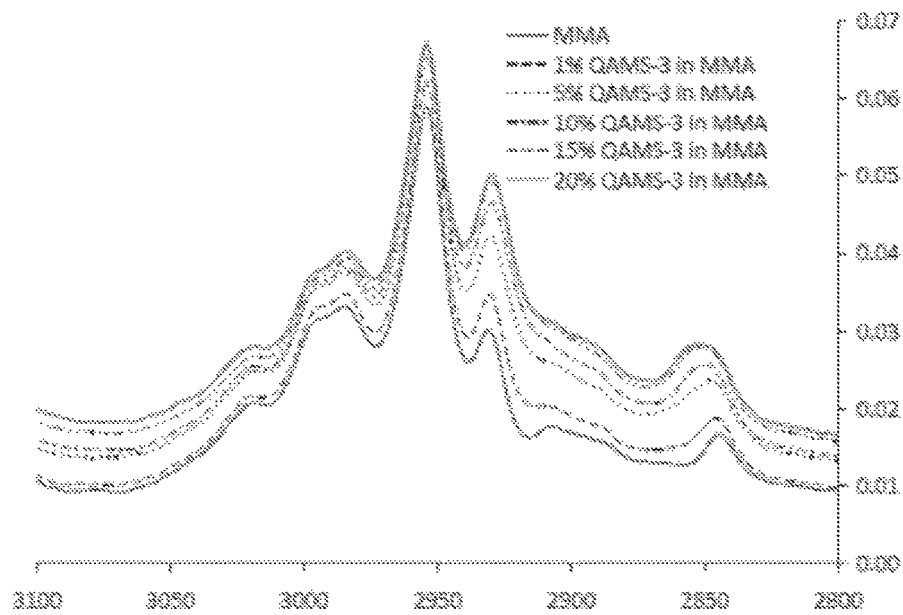
Figure 6C:
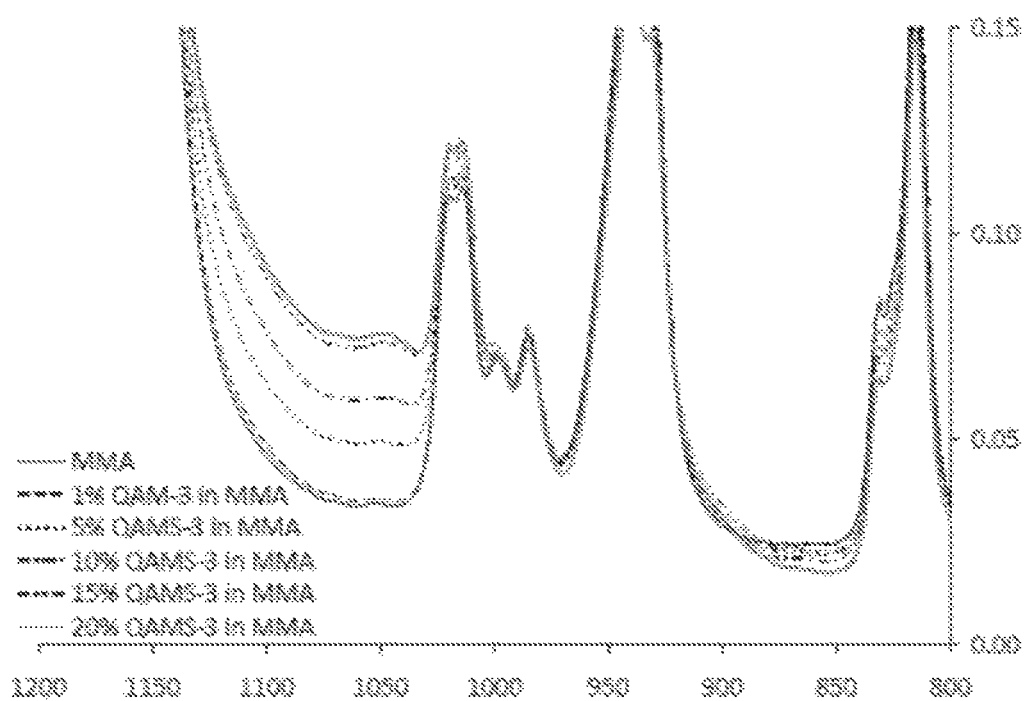

The polymers prepared, as shown in Table 9, were stable and did not form precipitate. The FTIR spectra for the series are shown in FIGS. 6A, 6B, and 6C.

Example 14: Incorporation to Polymers

A composition of the invention (compound of formula IV sorbed at 2% on silica) was prepared in accordance with the Table 10:

TABLE 10

| | Part B (pounds) | Part A (pounds) |
|---|---|---|
| Huber 103 precipitated silica | 10 | |
| Water (pH 10) | 20 | 0.52 |
| Siquat 5772 @ 72% | | 2.48 |
| MPTMS | | 0.2 |
| TEOS | | 0.172 | where:
TEOS=tetraethoxy silane
MPTMS=methacryloxypropyl trimethoxysilane
Siquat 5772=octadecyldimethyl trimethoxysilylpropyl ammonium chloride (at 72%)

Part A: Siquat 5772, TEOS and MPTMS were placed in a beaker with agitation. Water at pH 10 was added drop wise allowing mixing for 60 minutes.

Part B: Huber 103 precipitated silica was dispersed in deionized water adjusted to a pH of 10 with sodium hydroxide.

Part A was slowly added to Part B under constant agitation. This was allowed to mix for 60 minutes. The solution was weighed; poured into a shallow glass dish, place in an air circulating oven at 45° C. for 24 hours. The dried powder was removed from the oven, reweighed, broken up and sieved.

Powders were prepared and processed into a 20% master batch compound in an ethylene-methyl acrylate carrier resin. All materials were batched together and fed into the rear of the extruder using the following equipment and process conditions:

Extruder: 2½" twin screw
Throughput: 250 lb/hr
Ratio: 40 to 1
Pelletizer: Underwater cut
Heats Profiles: Feed zone 50° F., Barrel heats 300° F., Die 400° F., Screen changer 350° F.

Two master batches were produced. A control master batch containing the product material carrier only and an ethylene-methyl acrylate (EMA) resin, and a product master batch containing a composition of the invention and EMA resin. Blown film samples, tubing 19"×0.002", were then produced using the control master batch at a 2% concentration and the master batch of the invention at a 2% and 4% concentrations.

The materials may also be processed using other equipment, such as Banbury mixers, kneaders, and any device that mixes resin with powders. Furthermore, this includes adding powder to resin reactor flake prior to pelletizing.

The mixes for the blown film samples were as follows:
Mix 1 Control:
97% Dow 2045G linear low density resin
2% control master batch
1% clip additive (95% linear low density polyethylene and 5% Erucamide master batch)
teaspoon purple color concentrate
Mix 2:
97% Dow 2045G linear low density resin
2% master batch of the invention
1% slip additive (95% linear low density polyethylene and 5% Erucamide master batch)
teaspoon blue color concentrate
Mix 3:
93% Dow 2045G linear low density resin
6% master batch of the invention
1% slip additive (95% linear low density polyethylene and 5% Erucamide master batch)
teaspoon blue color concentrate Film samples were produced using a blown film, groove fed extruder:
Screw: 55 mm
Die: 4"
Die Gap: 55 mil
Heat Profiles:
Zone 1: 400° F.
Zone 2: 420'F
Zone 3: 400° F.
Screen Changer: 400° F.
Lower die: 400*F
Upper die: 400° F.
Pressure: 4800 psi
RPM: 2500

In addition to compounding the powders into resins as a master batch, these powders can also be mixed into powder or liquid thermosetting systems. Examples of suitable thermosetting plastics and polymers for use, including filled, unfilled, and blends, such as, for example, epoxy, polyester, alkyd, diallyl phthalate, melamine, polybutadiene, phenolic, silicone, urea, urethane, imide, or a mixture thereof.

Example 15: Preparation of Representative Compound of Formula IV

A mixture was prepared in the ratio of TEOS:6030:5772=1:3:1, specifically:
TEOS: 10.417 g
Z-6030: 37.27 g
5772: 34.465 g
in a container with magnetic bar stirring @~200 rpm. Water (pH 10, 1:3:1:48) (43.2 mL) was added. The mixture was permitted to hydrolyze and condense for at least 6 hours or overnight. The hydrolyzed and condensed product was heated at 100° C. for about 2 hours. The reaction was monitored using FTIR spectra. Si—O—Si bonds in the silicate network exhibit a broad band from ~1130 cm$^{-1}$ to ~1030 cm$^{-1}$, depending on the degree of polymerization (ratio of cyclic and linear Si—O—Si determine the profile of this area, e.g. peaking). For QAMS-3 (compound of Formula IV with three R$^a$ groups), we will get peak at 1040 cm$^{-1}$ after the reaction completes (See Deng et al., *Chem Mater* 1995, 7:2259-2268).

The compound of formula IV (QAMS) was dissolved into different quantities of MMA monomer and cured:
QAMS-MMA comonomer groups containing 0 (control), 1, 5, 10, and 15% by weight of QAMS:
QAMS 0 g—MMA 20 g
QAMS 0.2 g—MMA 19.8 g
QAMS 1 g—MMA 19 g
QAMS 2 g—MMA 18 g
QAMS 3 g—MMA 17 g Example 16: Incorporation of Compounds of Formula IV into Dental Adhesives and UV Curing Thereof The following tables show the preparation of the compound of formula IV (components added in the order listed) and the subsequent UV curing of the materials with a photoinitiator and synergist:

| | |
|---|---|
| TEOS | 2.08 g |
| Z-6030 | 7.44 g |
| 5700 @ 42% | 11.8 g |
| | (4.98 g) |
| Water (pH = 2) | 1.8 g |
| Initial observation | 1.8 g |
| | clear solution |
| Photoinitiator (camphorquinone) | 0.18 g |
| Ethyl-4-(dimethylamino)benzoate | 0.18 g |
| Initial observation | yellow |
| Observation after ~5 months | gel |
| Rely-X | 1 gram |

|  |  |  |
|---|---|---|
| Denmat A1 | | |
| MMAP A2 | | |
| K-33 drops | preapply | |
| UV cure | x | |
| between glass/Si wafer | | 3 g |
| | 1 | 2 |
| | x | x |

Example 17: Removal of Alcohol by-Product

This example shows the preparation of compound of formula IV where the polymers were heated to remove the alcohol by-products from the reaction chemistries. Therefore, the final products contain no water or alcohol in the final product. The preparation is shown is Table 11 below. All quantities are in grams, except where noted.

TABLE 11

|  | 17-1 | 17-2 | 17-3 | 17-4 | 17-5 | 17-6 |
|---|---|---|---|---|---|---|
| HEMA | | | | 30.46 | 7.6 | 76 |
| TEGDMA | 33.79 | | | | | |
| Bis-GMA | | 33.79 | 15.23 | | | |
| TEOS | 2.08 | 2.08 | 8.32 | 16.64 | 4.16 | 41.6 |
| Z-6030 | 7.44 | 7.44 | 29.2 | 28.4 | 14.6 | 146 |
| 5700 @ 42% | 11.8 | 11.8 | | | | |
| 5772 @ 72% | | | 27.5 | 27.5 | 13.75 | 137.5 |
| Mix, min | 60 | 60 | 60 | 60 | 60 | 60 |
| Water(pH = 2) | 3.6 | 3.6 | 3.6 | 7.2 | 27 | 270 |
| Mix (hours) | 24 | 24 | 24 | 24 | | |
| Heat, 70° C. | 2 hrs | 3 hrs | 1 Hr/90 C. | | | |
| Removed | 12 | 9.04 | 20.97 | | | |

Example 18

This example shows the preparation of compound of formula IV co-reacted with a comonomer of methyl methacrylate (MMA) or urethane dimethacrylate (UDMA). All quantities are in grams, except where noted.

| Sample | K-100 | K-101 |
|---|---|---|
| MMA comonomer | 54.18 | |
| UDMA comonomer | | 54.18 |
| TEOS | 2.08 | 2.08 |
| Z-6030 | 2.26 | 2.26 |
| 5772 @ 72% | 14.88 | 14.88 |
| | (20.6) | (20.6) |

Examples 19-23: Compositions with Fillers

These examples shows the preparation of compound of formula IV with various fillers All quantities are in grams, except where noted.

Example 19: Silica

|  | 2A | 2B | 3A | 3B | 4A | 4B |
|---|---|---|---|---|---|---|
| Huber 103 | | | | | | 25 |
| Huber 250 | | 25 | | 25 | | |
| Water pH 10 | 5 | 100 | 1.3 | 100 | 0.5 | 100 |
| 5772 @ 72% | 2.08 | | 6.2 | | 6.3 | |
| VTM | 0.5 | | 0.43 | | | |
| TEOS | | | 0.5 | | 0.5 | |
| | mix into 2B | | mix into 3B | | mix into 4B tooth paste | |
| initial weight | | 120.5 | | 150.7 | | 129.2 |
| final weight | | 28.25 | | 32.44 | | 32.49 |

Example 20

|  | 3A | 3B | B | A |
|---|---|---|---|---|
| Huber 103 | | | 25 | 10# |
| Water pH 10 | 1.3 | 100 | | 20# 0.52# |
| 5772 @ 72% | 6.2 | | | 2.48# |
| Z-6030 | 0.43 | | | 0.2# |
| TEOS | 0.5 | | | 0.172# |

Example 21: Silica

|  | 2A | 2B | 3A | 3B |
|---|---|---|---|---|
| Huber 250 | | 25 | | 25 |
| Water pH 10 | 5 | 100 | 1.3 | 100 |
| 5772 @ 72% | 2.08 | | 6.2 | |
| VTM | 0.5 | | 0.43 | |
| TEOS | | | 0.5 | |
| | mix into 2B | | mix into 3B | |

Example 22

|  | 113-2 | | 311-2 | | 113-8 | |
|---|---|---|---|---|---|---|
|  | B | A | B | A | B | A |
| Huber 103 | 15 # | | 15 # | | 15 # | |
| Water pH 10 | 25# | 18.36 | 25# | 14.04 | 25# | 73.44 |
| 5700 @ 42% | | 100.3 | | 230 | | 401.2 |
| Z-6030 | | 63.24 | | 16.12 | | 252.96 |
| TEOS | | 17.68 | | 13.52 | | 70.72 |

Example 23

|  | KAO 113-2 | | KAO 311-8 | |
|---|---|---|---|---|
|  | B | A | B | A |
| Kaogloss | 15 | | 15 | |
| Water pH = 10 | 25 | 108 | 25 | 108 |
| 5700 @ 42% | | 590 | | 1770 |
| | | (250) | | (743) |
| Z-6030 | | 372 | | 124 |
| TEOS | | 104 | | 104 |

-continued

| | TRO 113-2 | | TRO 311-8 | |
|---|---|---|---|---|
| | B | A | B | A |
| Tronox CR-813 | 15 | | 15 | |
| Water pH = 10 | 25 | 108 | 25 | 108 |
| 5700 @ 42% | | 590 (250) | | 1770 (743) |
| Z-6030 | | 372 | | 124 |
| TEOS | | 104 | | 104 |

| | HYD 113-2 | | HYD 311-8 | |
|---|---|---|---|---|
| | B | A | B | A |
| Hydrol 710 | 15 | | 15 | |
| Water pH = 10 | 25 | 108 | 25 | 108 |
| 5700 @ 42% | | 590 (250) | | 1770 (743) |
| Z-6030 | | 372 | | 124 |
| TEOS | | 104 | | 104 |

| Abbreviation | MW | Description | Supplier |
|---|---|---|---|
| Catalyst/photoinitiator | | Camphorquinone | Esstech |
| Synergist | | Ethyl-4-(dimethylamino) benzoate | Esstech |
| TEOS | 208 | Tetraethoxy silane | Dow Corning Corp |
| Z-6030 | 248 | methacryloxypropyltrimethoxy silane | Dow Corning Corp |
| Z-6040 | 236 | glycidoxypropyltrimethoxy silane | Dow Corning Corp |
| VEO | 190 | vinyltriethoxy silane | Dow Corning Corp |
| VME | 280 | vinyl(tris-(2-methoxyethoxy) silane | Dow Corning Corp |
| VMO | 148 | vinyltrimethoxy silane | Dow Corning Corp |
| TBT | 340 | Titanium n-butoxide | Gelest |
| TPZr @ 70% | 327 | Zirconium n-propoxide, 70% in n-propanol | Gelest |
| Ti MAE @70% | 422 | Titanium trimethacrylate methoxyethoxyethoxide, 70% in methoxydiethyleneglycol | Gelest |
| Z-6341 (NOTES) | 234 | n-octyltrimethoxy silane | Dow Corning Corp |
| Z-6020 | 226 | aminoethylaminopropyltrimethoxy silane | Dow Corning Corp |
| mptes | 290 | methacryloxypropyltriethoxy silane | Gelest |
| E 5772 @ 72% | 538 | N-(3-triethoxysilyl propyl)-N-octadecyl-N,N-dimethyl) ammonium chloride 70% solution in SDA 40B ethanol | Wm Barr |
| 5700 @ 42% | 496 | N-(3-trimethoxysilyl propyl)-N-octadecyl-N,N-dimethyl) ammonium chloride 42% solution in methanol | Aegis |
| HEMA | | 2 hydroxy ethyl methacrylate | Esstech |
| HDDMA | | 1,6 hexanediol dimethacrylate | Esstech |
| Bis-GMA | | Bisphenol A Bix(2-hydroxy-3-methacrylaoxyproply)ether | Esstech |
| TEGDMA | | triethylene glycol dimethacrylate | Esstech |
| MMA | | methyl methacrylate | Esstech |
| UDMA | | urethane dimethacrylate | Esstech |
| Kaogloss | | Hydrous kaolin clay | Thiele |
| Tronox CR-813 | | Titanium dioxide | Tronox |
| Hydrol 710 | | Aluminum trihydrate | Huber |

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A composition, comprising:
   at least one polymer selected from the group consisting of natural rubber, synthetic rubber, thermoplastic polymer, thermosetting polymer, and combinations thereof; and
   at least one compound of formula IV:

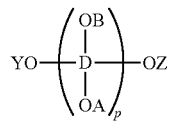

IV wherein:
p is 1 to about 5;
D is independently Si, Ti, Al, or Zr;
A, B, Y, and Z are each independently selected from the group consisting of H, $C_1$-$C_8$alkyl, trifluoro-substituted ($C_1$-$C_8$)alkyl,

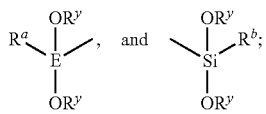

E is independently Si or Ti;
$R^a$ is independently a functional group comprising at least one curing group selected from the group consisting of acrylate, methacrylate, (C$_2$-C$_8$) alkenyl, glycidyloxy, ester, amino, acrylamide, methacrylamide, isocyanato, amino acid, nucleic acid, and mercapto(C$_1$-C$_6$)alkyl;

R$^b$ is independently

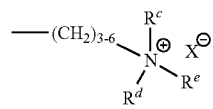

wherein:
R$^c$ is (C$_1$-C$_2$)alkyl;
R$^d$ is (C$_1$-C$_2$)alkyl or phenyl;
R$^e$ is (C$_6$-C$_{22}$)alkyl;
X$^-$ is an anion selected from the group consisting of chloride, bromide, fluoride, iodide, sulfonate, and acetate;
each R$^y$ is, independently, H, (C$_1$-C$_8$)alkyl, or trifluoro-substituted (C$_1$-C$_8$)alkyl; and
wherein at least one of A, B, Y, and Z is

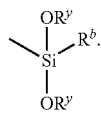

2. A composition of claim 1,
wherein at least one of A, B, Y, and Z is

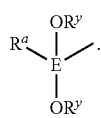

3. A composition of claim 1,
A, B, Y, and Z are each independently selected from the group consisting of H,

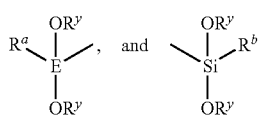

4. A composition of claim 1,
wherein R$^b$ is independently —(C$_3$-C$_6$ alkylenyl)-(dimethyl)-(C$_6$-C$_{22}$alkyl) quaternary ammonium chloride or —(C$_3$-C$_6$ alkylenyl)-(methyl)-(phenyl)-(C$_6$-C$_{22}$alkyl) quaternary ammonium chloride.

5. A composition of claim 1,
wherein R$^b$ is —(C$_3$ alkylenyl)-(dimethyl)-(C$_{18}$alkyl) quaternary ammonium chloride.

6. A composition of claim 1,
wherein R$^y$ is (C$_1$-C$_2$)alkyl.

7. A composition of claim 1,
wherein R$^a$ is acrylate, methacrylate, or vinyl.

8. A composition of claim 1, further comprising:
at least one filler;
wherein said one compound of formula IV is sorbed on said filler.

9. A composition of claim 1,
wherein said thermoplastic polymer is a polyethylene, polypropylene, polyvinyl chloride, polyester, acrylic, methacrylic, or a copolymer or mixture thereof.

10. A composition of claim 1,
wherein said thermosetting polymer is an epoxy, polyester, alkyd, diallyl phthalate, melamine, polybutadiene, phenolic, silicone, urea, urethane, imide, or a mixture thereof.

11. A composition of claim 1, further comprising:
at least one filler;
wherein said one compound of formula IV is sorbed on said filler.

12. A composition of claim 1,
wherein said polymer is selected from the group consisting of:
acrylonitrile-butadiene-styrene;
acetal;
acrylic;
methacrylic;
cellulosic;
ethylene copolymer;
fluoropolymer;
nylon;
polyarylate;
polyarylsufone;
polybutylene;
polycarbonate;
polycarbonate-acrylonitrile-butadiene-styrene alloy;
polyester;
polyetheretherketone;
polyetherimide;
polyethersulfone;
polyethylene;
ionomer;
polymethylpentene;
polyphenylene oxide;
polyphenylene sulfide;
polyimide;
polypropylene;
polystyrene;
polysulfone;
polyurethane;
polyvinyl chloride;
chlorinated polyvinyl chloride;
polyvinyl chloride-acrylic;
polyvinyl chloride-acrylonitrile-butadiene-styrene;
styrene acrylonitrile;
styrene maleic anhydride;
thermoplastic elastomer;
thermoplastic vulcanizate; and
copolymers and mixtures thereof.

13. A polymeric article, comprising:
said composition of claim 1 or a polymerized residue of said composition of claim 1.

14. A polymeric article of claim 13,
wherein said polymeric article is prepared by blown film, cast film, profile extrusion, sheet extrusion, foam extrusion, roto-molding, injection molding, injection molding, blow molding, foamed, coating, or a combination thereof.

15. A polymeric article of claim 13,
wherein said polymeric article is a film, sheet, container, foam container, bottle, crate, plastic part, toy, pipe, foam insulation, panel, plastic lumber, implantable device, or prosthetic device.

16. A coating material, comprising:
said composition of claim 1.
17. A cured coating, comprising:
the polymerized residue of said composition of claim 1.

* * * * *